US007678328B1

(12) United States Patent
Secrist et al.

(10) Patent No.: US 7,678,328 B1
(45) Date of Patent: Mar. 16, 2010

(54) ROTATABLE BOMB

(75) Inventors: James F. Secrist, Midland, MI (US); Robert J. Hite, Jr., Pinconning, MI (US); Gregory C. Miiller, Pinconning, MI (US); Theodore W. Selby, Midland, MI (US); William A. Atkins, Bay City, MI (US)

(73) Assignee: Tannas Company, Midland, MI (US)

( * ) Notice: Subject to any disclaimer, the term of this patent is extended or adjusted under 35 U.S.C. 154(b) by 1396 days.

(21) Appl. No.: 11/006,456

(22) Filed: Dec. 7, 2004

Related U.S. Application Data

(60) Provisional application No. 60/527,725, filed on Dec. 8, 2003.

(51) Int. Cl.
*G01N 33/00* (2006.01)
(52) U.S. Cl. ............... 422/51; 422/50; 422/68.1; 422/99; 422/102; 422/104
(58) Field of Classification Search ............ 422/50, 422/51, 68.1, 99, 102, 104
See application file for complete search history.

(56) References Cited

OTHER PUBLICATIONS

Lawler Mfg. Corp., RBOT Test Device Web Site Communication With E-mail of Aug. 4, 2006 From Theodore W. Selby.
Secrist et al., U.S. Appl. No. 60/527,725, filed Dec. 8, 2003 A.D.
Tannas Company, "Tannas 'Quantum,'" web site print out, Aug. 23, 2004 A.D.
Tannas Company, "Tannas 'Quantum,'" brochure, Mar. 6, 2004 A.D.
Tannas Company, "Precision-Proven Instruments for Lubricant and Fluids Testing," catalog, cover and pp. 22-23.
Southwest Research Institute, "Rotating Bomb Oxidation Test (RBOT)," brochure.
Koehler Co., "K70200 Oxidation Stability Bath, RBOT/TFOUT," web site printout, Jan. 7, 2005 A.D.
ASTM D 2272-02.
ASTM D 4742-02a.

*Primary Examiner*—Sam P Siefke
(74) *Attorney, Agent, or Firm*—Christopher John Rudy

(57) ABSTRACT

Rotatable bomb device includes a housing with a hollow interior for receipt of a rotatable component to a vessel, and support for the component in the interior; and the component for such receipt and support in the housing. The device may be employed as a reactor or in test methods, for example, methods such as oxygen uptake tests analogous or equivalent to the ASTM-D-2272 and ASTM-D-4742 test methods.

18 Claims, 40 Drawing Sheets

FOR HEAT-LOSS PROTECTION
& SAFETY BY AVOIDING BURNS
FROM HOT LID

MAY SILK SCREEN TOP OF COVER WITH INDICIA, E.G., LOGO

PRESS FIT INTO COVER OPENING

NOTE:

SEE PRINT 7 0 8 4

FOR ASSEMBLY DETAILS

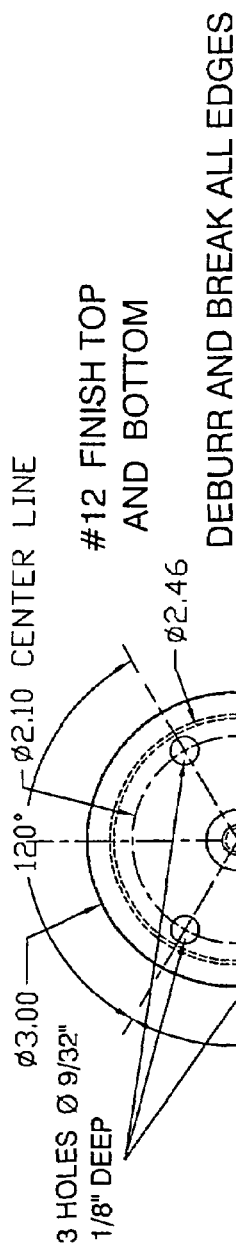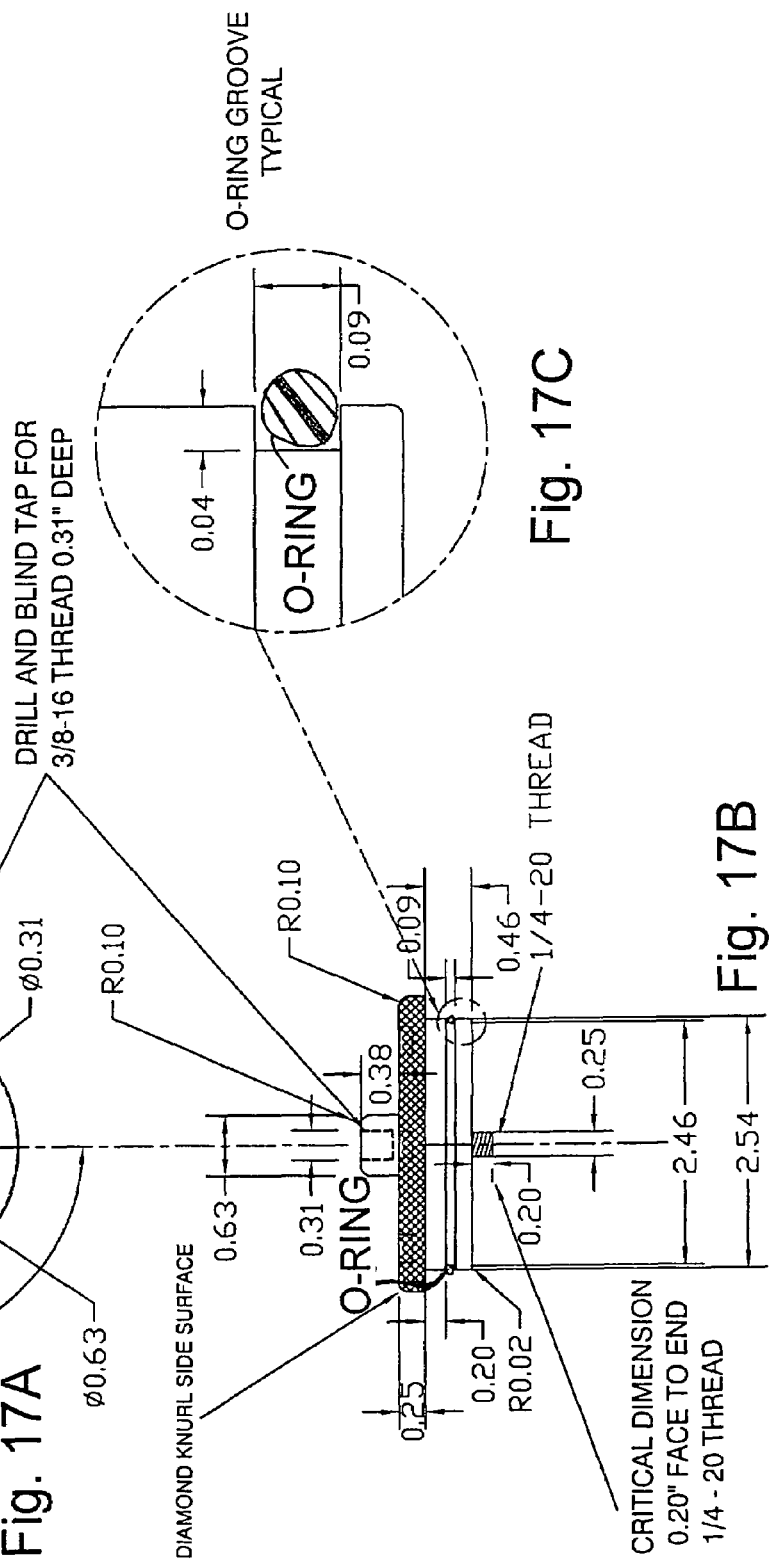

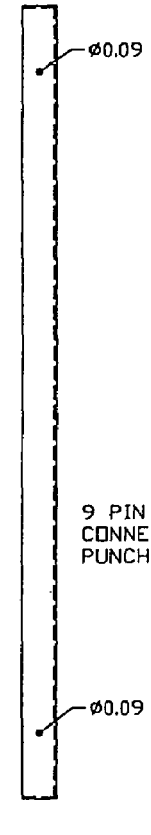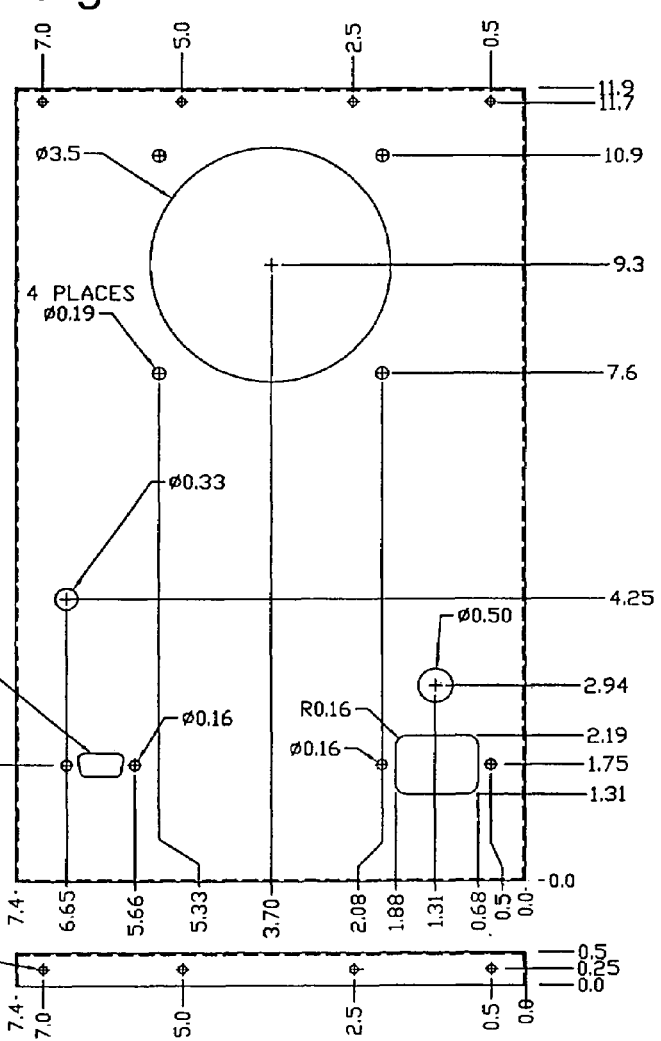

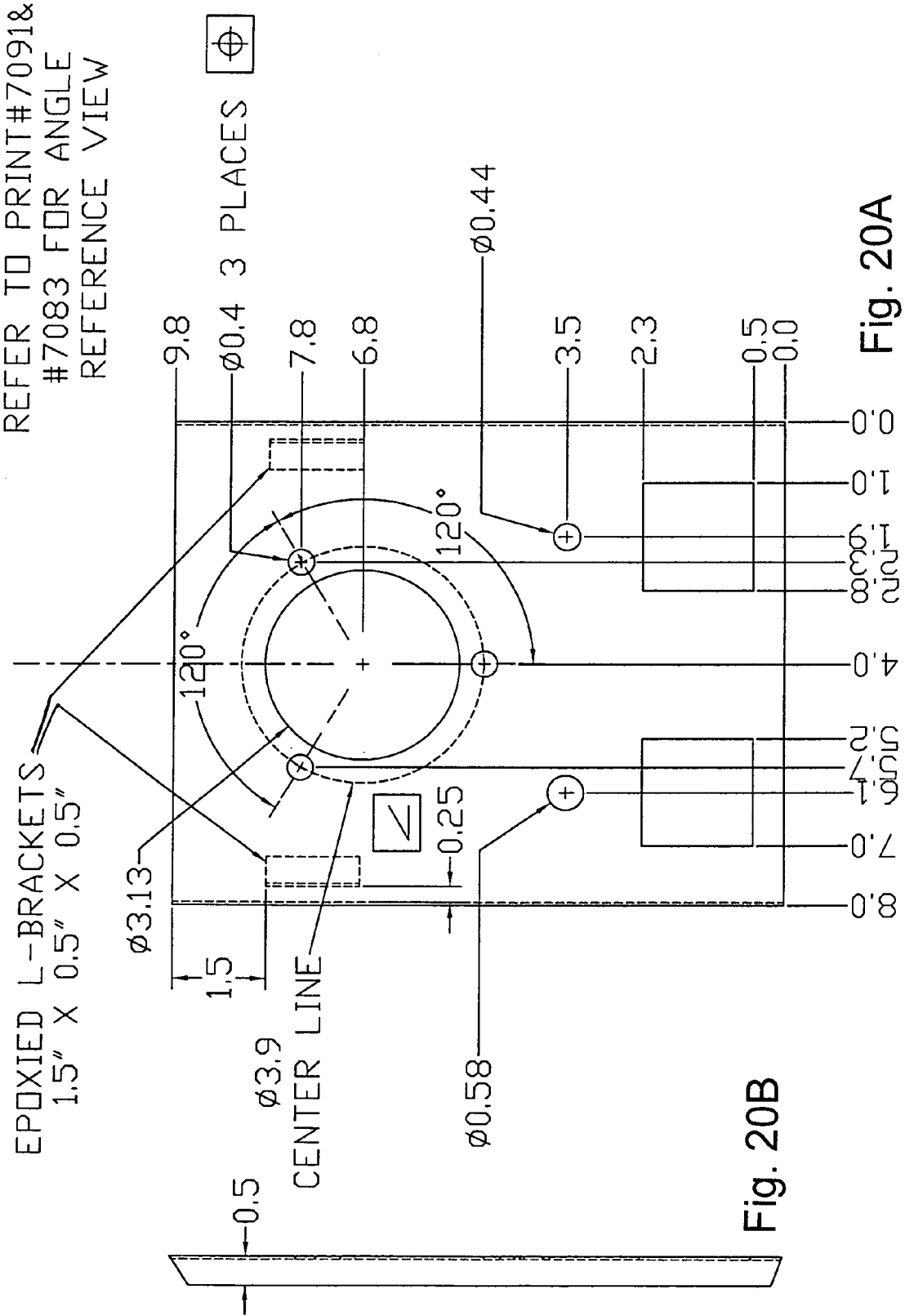

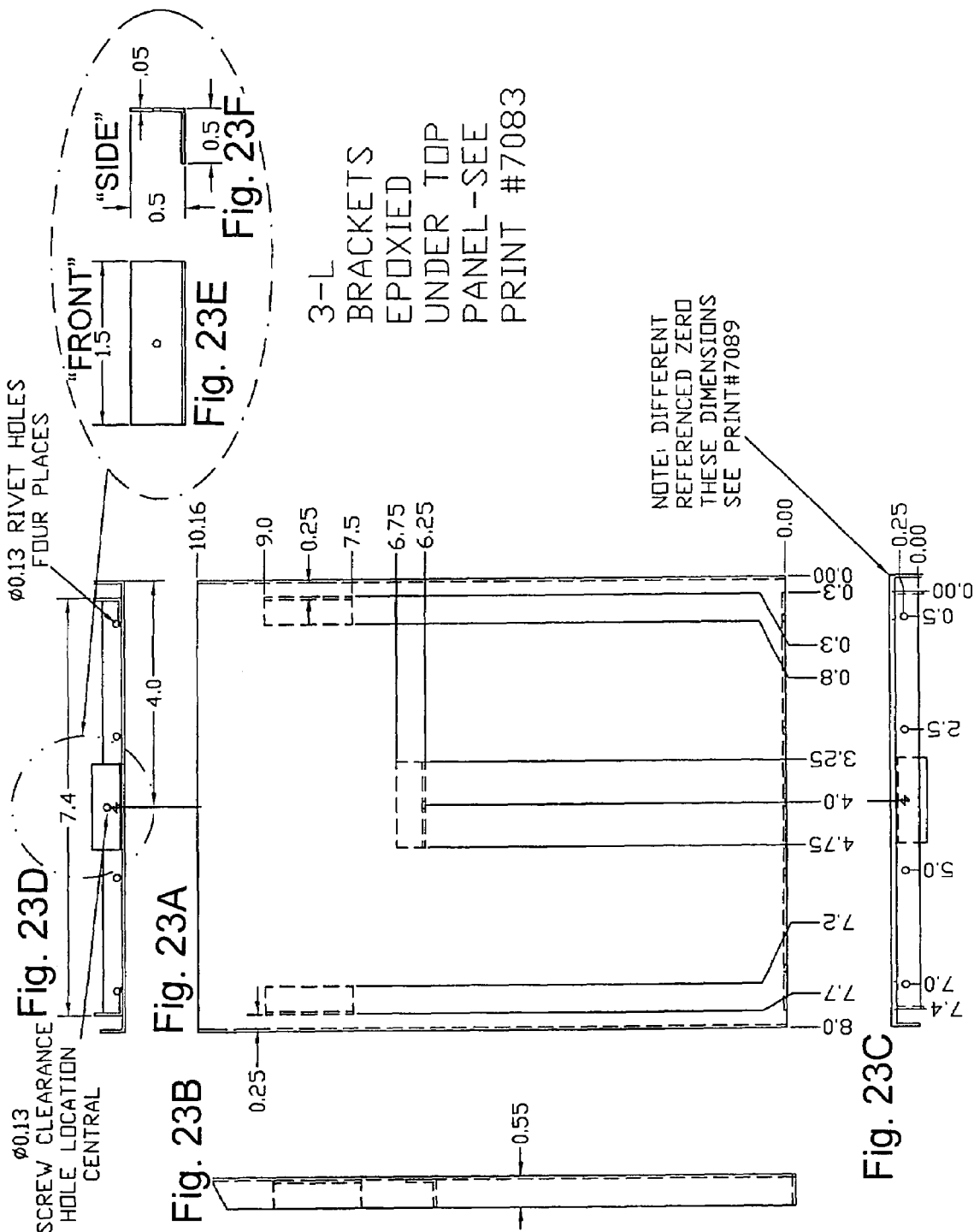

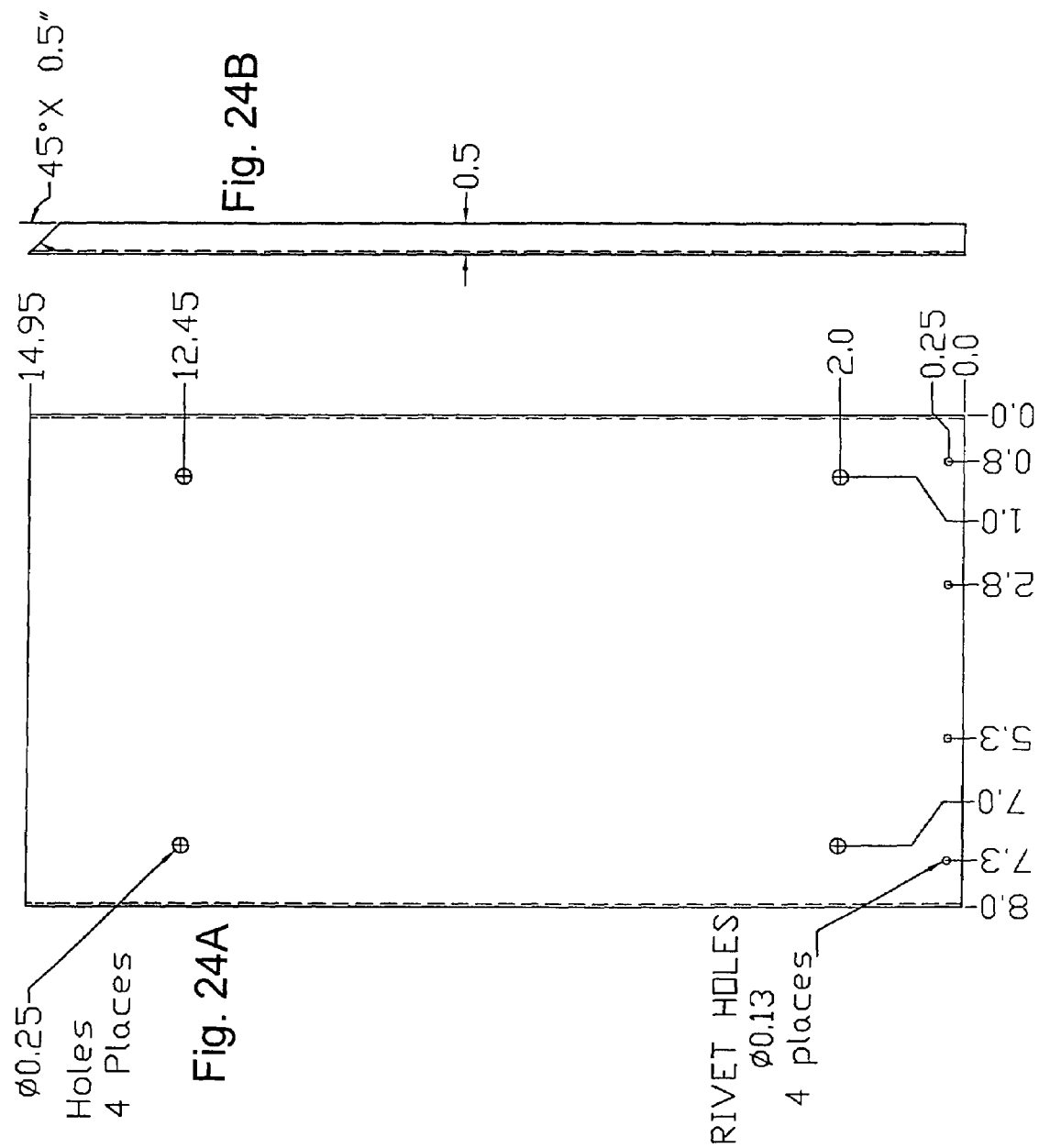

NOTES: ALL ENGLISH DIMENSIONS TO BE MARKED IN [X.XX].
Ⓐ PART NO. WAS TF-5002

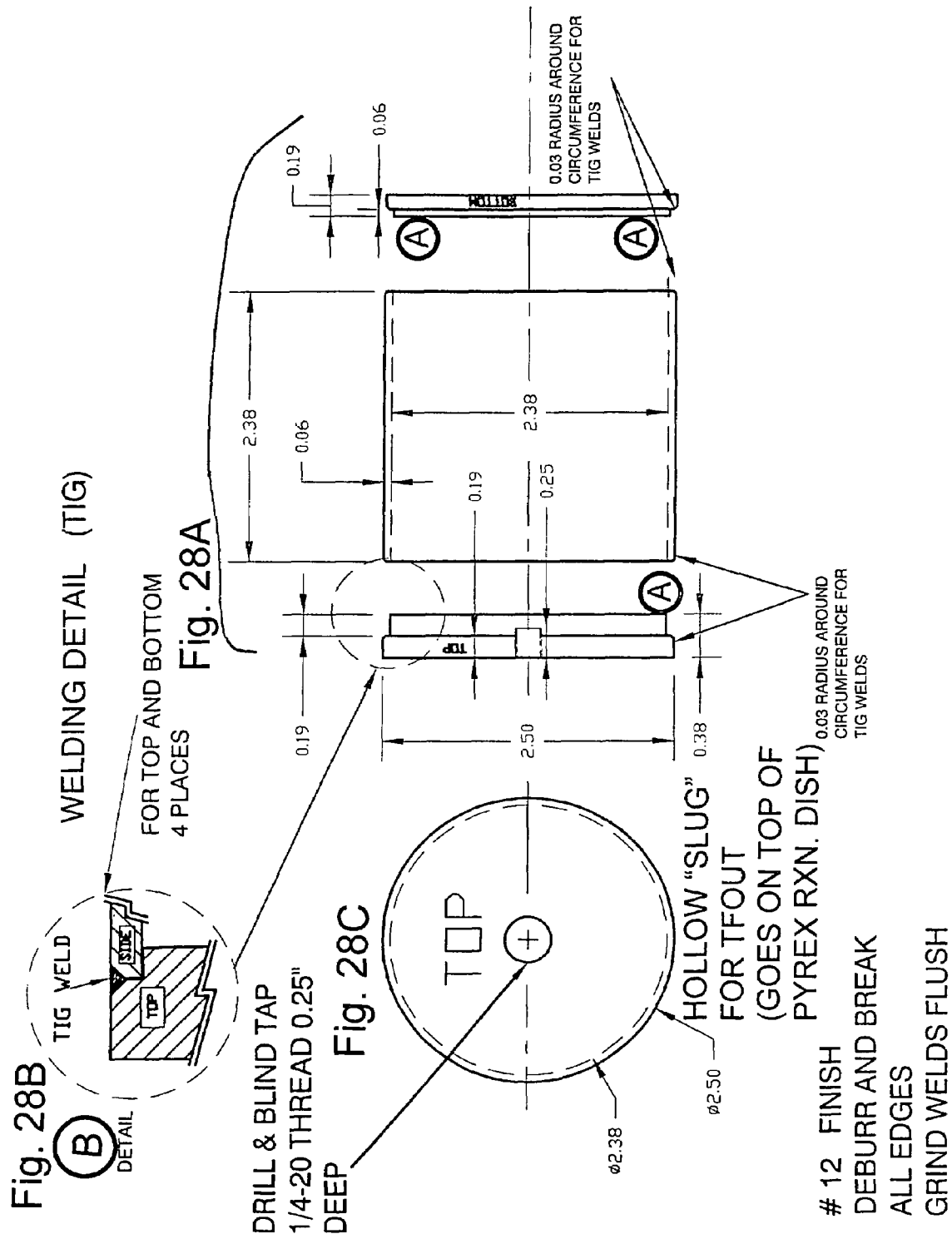

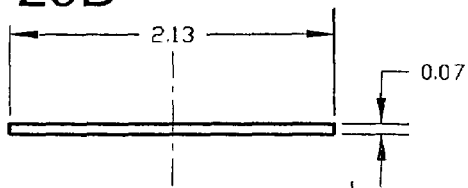
Fig. 29D
Cup Lid. Place magnet backing on pins and tig weld into top of inner cup for seal. Keep heat low, below 200°C. Grind top flush to # 12 Finish
REFER TO PRINT 7110 FOR ASSEMBLY
Fig. 29C
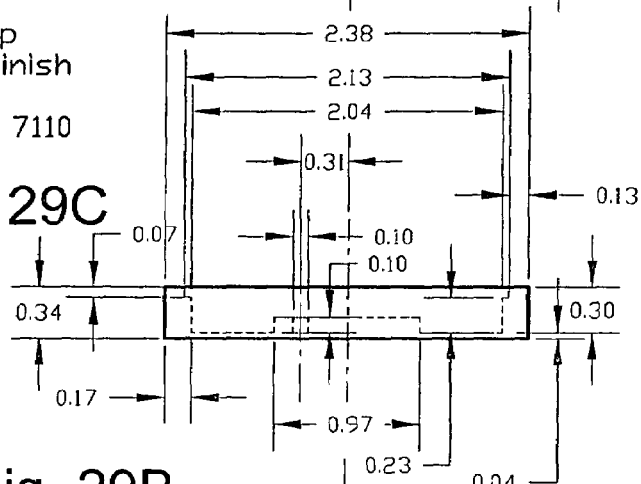
Fig. 29B
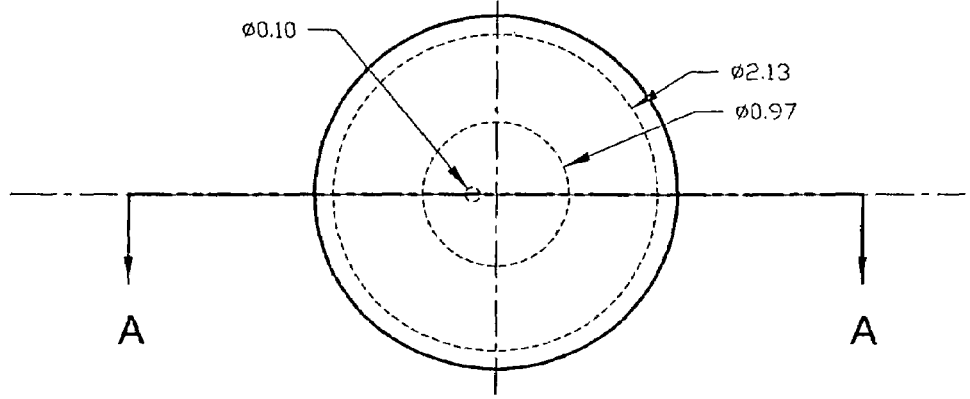
Fig. 29A
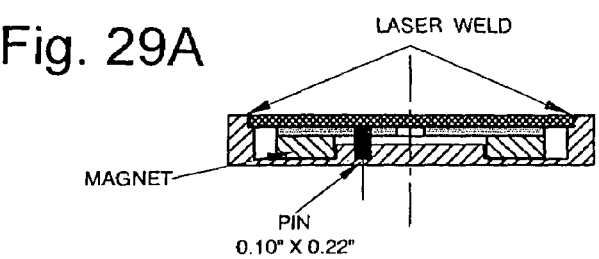
SECTION A - A
ASSEMBLY VIEW

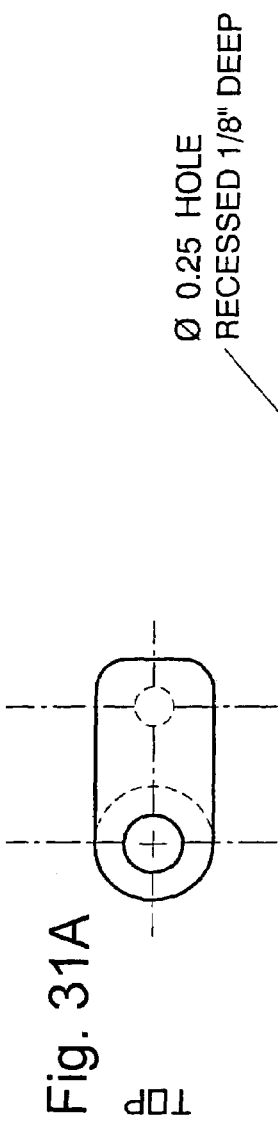
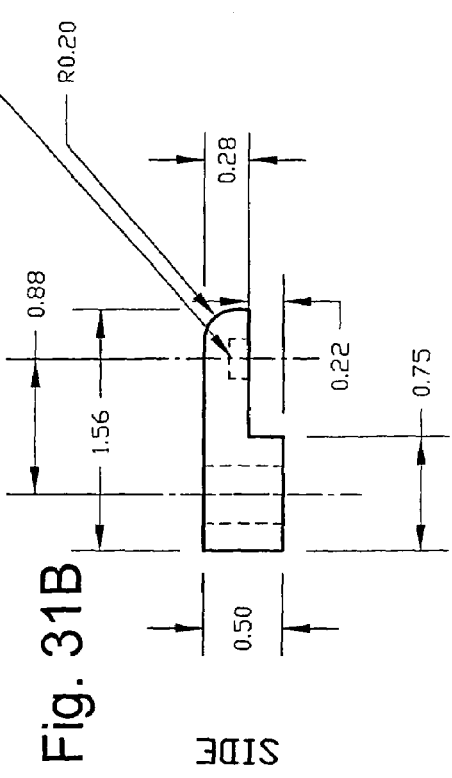
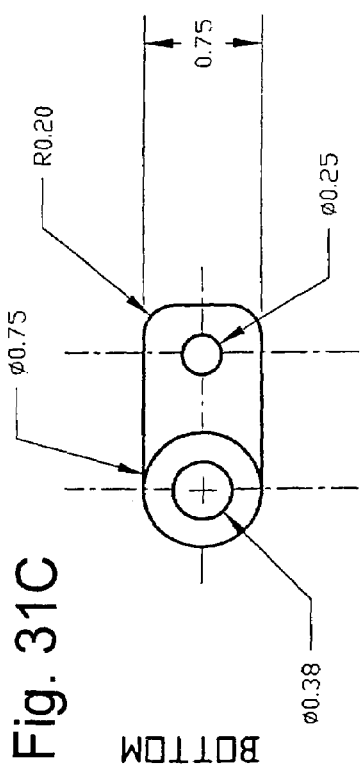
Fig. 31A TOP
Fig. 31B SIDE
Fig. 31C BOTTOM
L-CLAMPS
DEBURR AND BREAK ALL EDGES
12 BRUSH FINISH

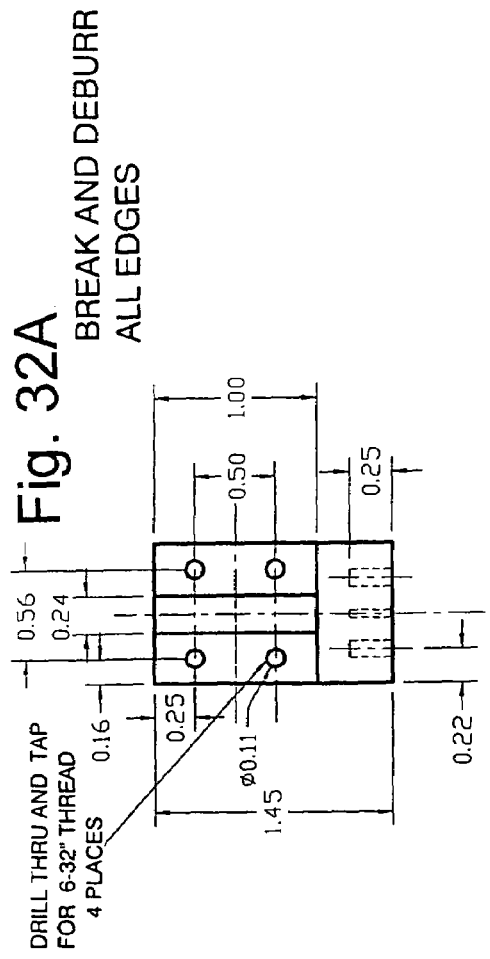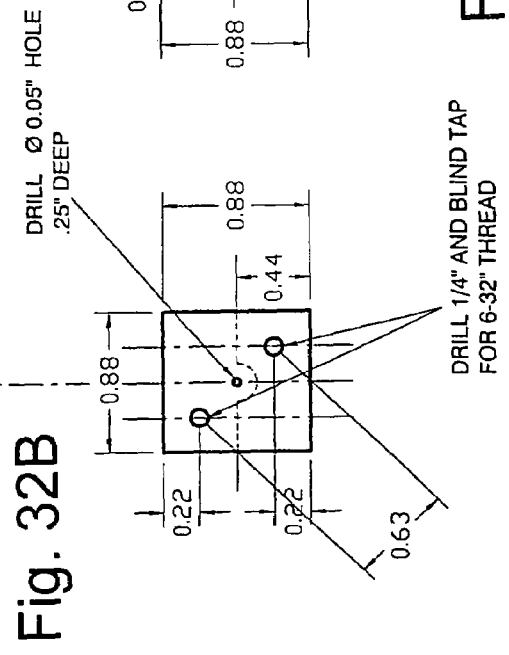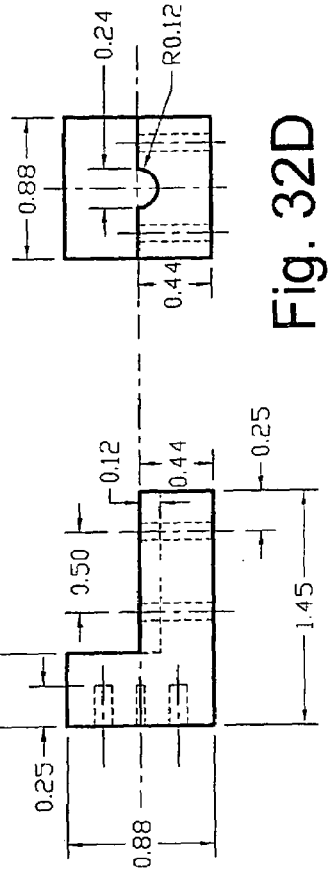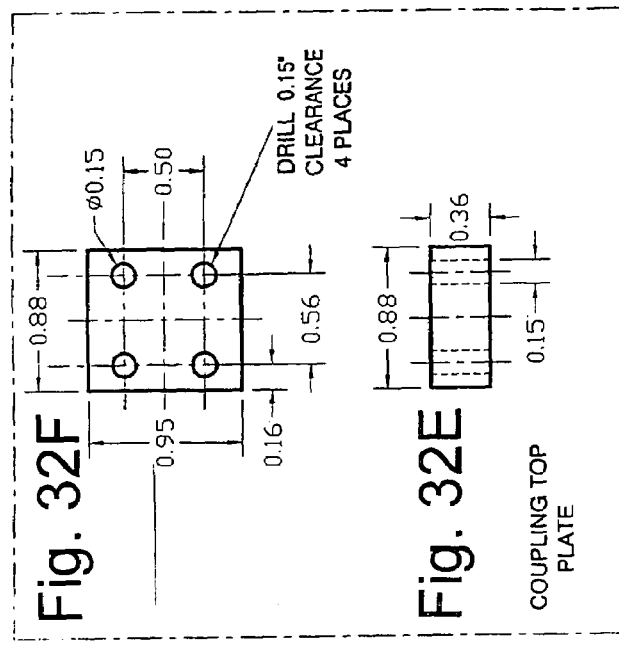

NOTE: BREAK ALL EDGES AND CORNERS DEBURR

SEE PRINT: 7 1 0 5 FOR CUTS, BENDS, AND SPECIFIC DIMENSIONS

Fig. 35B
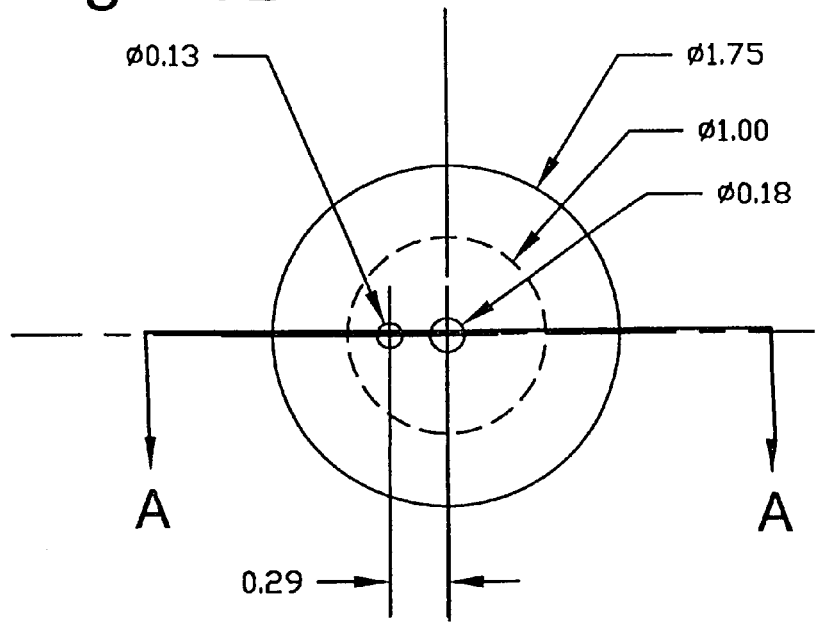
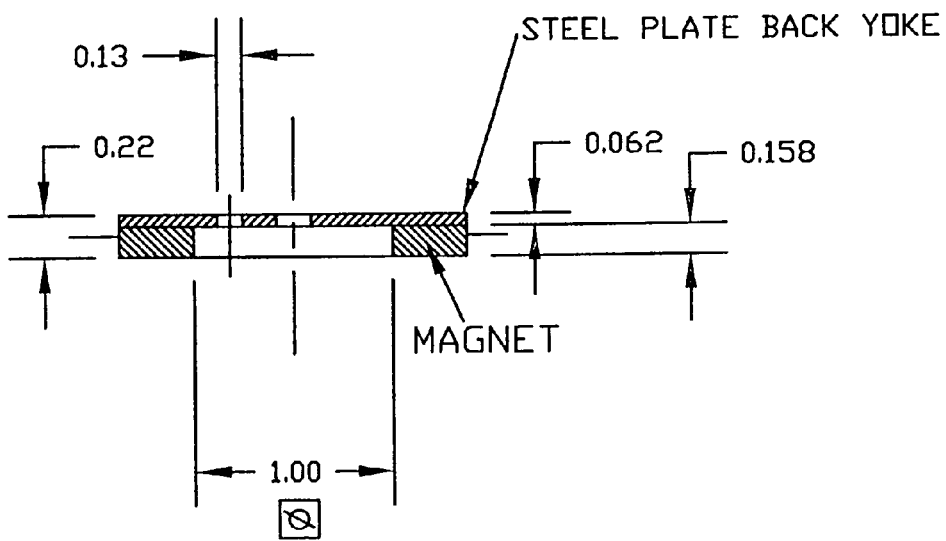
Fig. 35A
SECTION A-A

SECTION A-A

① REFER TO PRINT 7 1 0 1
(INNER CUP BOTTOM)
AND PRINT 7 0 8 2
(INNER CUP RING)
FOR THIS CUP
ASSEMBLY

③ BREAK AND DEBURR
ALL EDGES
12 FINISH

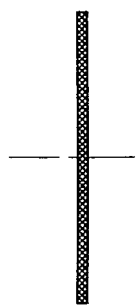

Fig. 37A

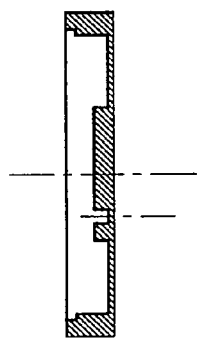

Fig. 37B

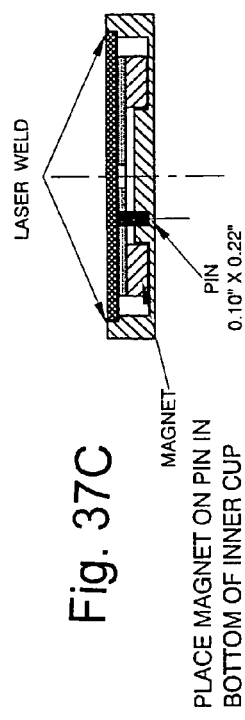

Fig. 37C

PLACE MAGNET ON PIN IN
BOTTOM OF INNER CUP

TIG WELD 0.07" COVER INTO TOP
OF INNER CUP FOR SEAL

KEEP HEAT LOW, BELOW 200° C

GRIND TOP FLUSH
TO # 12 FINISH

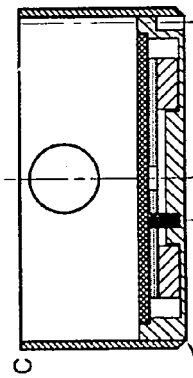

Fig. 37D

PRESS FIT ONTO CUP INSERT (PRINT 7101)
WITH THE HOLE AT TOP AS SHOWN. THE CUP IN
MUST HAVE THE WELDED SIDE UP WITH THE
BOTTOM FLUSH. DRILL 0.10" HOLES AFTER ASS
AND CHAMFER CIRCUMFERENCE 0.0625"

PRESS FIT FLUSH TO
BOTTOM
GRIND FLAT TO # 12
FINISH

ROTATABLE BOMB

This claims benefit under 35 USC 119(e) of patent application Ser. No. 60/527,725 filed on Dec. 8, 2003 A.D. The full specification of that application is incorporated herein by reference.

FIELD OF THE INVENTION

The present invention concerns a rotatable bomb device and a method of testing or reacting with the device.

BACKGROUND TO THE INVENTION

Various types of bomb test devices are known. Among these may be mentioned the Thin Film Oxygen Uptake Test (TFOUT) device from Tannas Company of Midland, Mich., and the Rotating Bomb Oxidation Test (RBOT) device from Southwest Research Institute of San Antonio, Tex., which are employed in the well known ASTM D-4742 and ASTM D-2272 test methods, respectively.

The TFOUT device utilizes twin stainless steel, rotating bomb reactors in gathering precise measurements of oil oxidation characteristics. It uses a single 3.25 gallon bath of heated oil for the reactors, and takes about half an hour to set up.

The RBOT device utilizes two stainless steel, rotating bomb reactors in gathering turbine oil oxidation data. It uses large, separate, heated oil baths for each reactor, and also takes about half an hour to set up.

Another device, from Koehler Co., is known, a TFOUT/RBOT device. These devices have 2-4 arm units per hot oil bath, and require all bombs to be finished before moving on. Removal of one bomb unit for cleaning affects other bomb(s).

Operators must be careful to not get harmed from the hot bath oil or its vapors. Also, the vapors can undesirably condense on surrounding equipment.

It would be desirable to improve upon such art.

A SUMMARY OF THE INVENTION

In general, the invention can provide a rotatable bomb device that comprises a housing with a hollow interior for receipt of a rotatable component to a vessel, and support for the component in the interior; and the component for such receipt and support in the housing. Among its utilities, the device may be employed as a reactor or in test methods, for example, methods such as oxygen uptake tests analogous, equivalent or equal to the ASTM D-2272 and ASTM D-4742 test methods.

Significantly, by the invention, versatility in rotating bomb devices is improved in kind. The device of the invention can be used in various reactions and testing methods. For example, the device may be employed in ASTM D-2272 testing and, with a change of its rotatable vessel in the same housing, ASTM D-4742 testing. Temperature control can be maintained at a high if not increased degree of accuracy and precision. The device of the invention can be much smaller than the TFOUT and/or RBOT test devices. Moreover, the problematic and costly liquid bath found in the TFOUT and RBOT devices is eliminated. Set up time can be reduced, and maintenance can be reduced, to include in comparison to that required for two separate TFOUT and RBOT devices.

Numerous further advantages attend the invention.

DRAWINGS ILLUSTRATIVE OF THE INVENTION

The drawings form part of the specification hereof. With respect to the drawings, which are not necessarily drawn to scale, the following is briefly noted:

Figure 6:
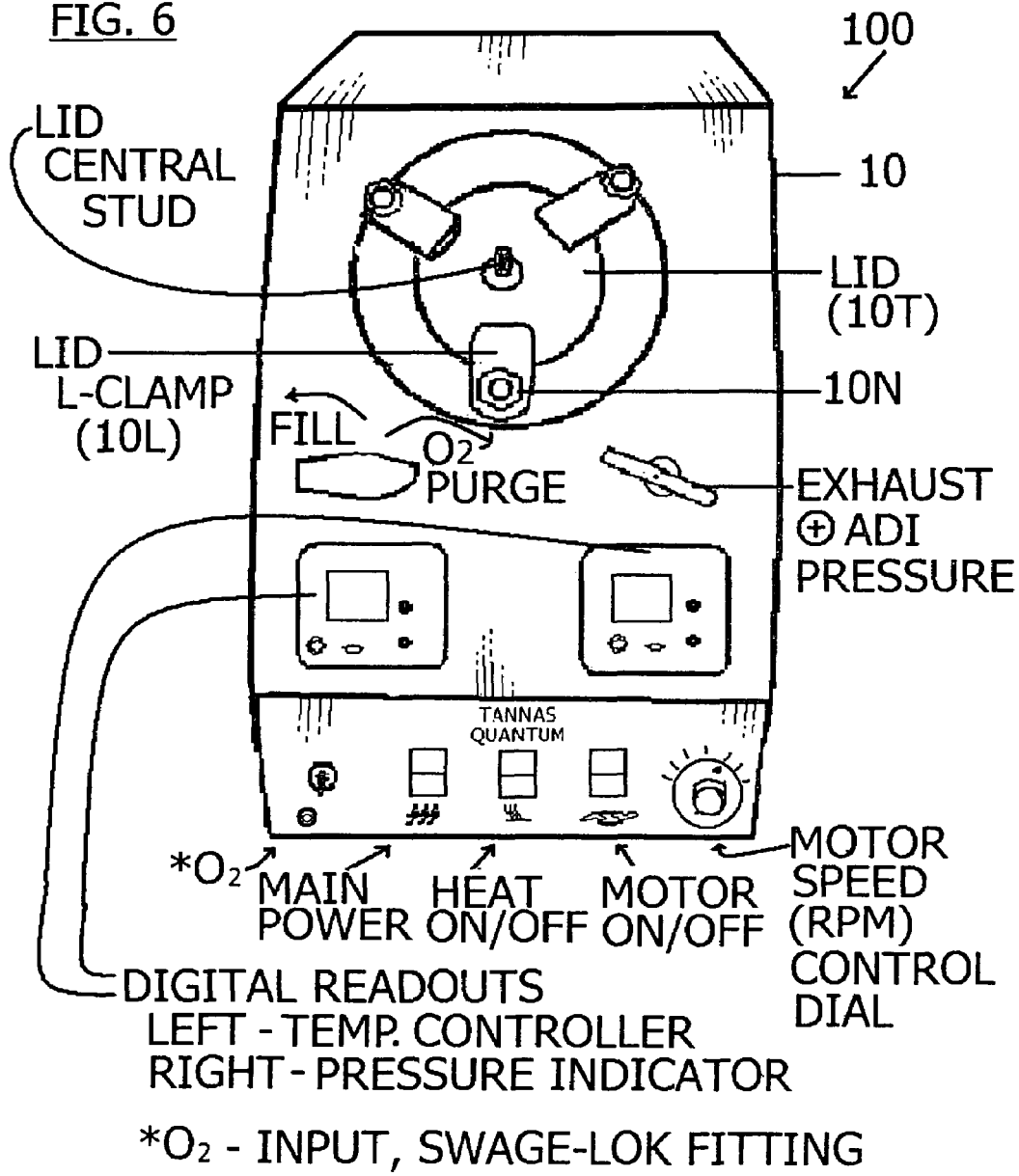
FIG. 6 is a front view of a preferred embodiment of a device of the invention.

FIG. 11-38 are print type plan views of components for a device such as that of FIG. 6. In general, dimensions are often in English units, e.g., linear inches, and may be considered to be approximate. These views are elaborated upon as follows:

FIGS. 11A, 11B, 11C, 11D and 11E are views (print #7080) of a reaction assembly made of #304 stainless steel (#304-SS) for the device.

FIGS. 12A, 12B, 12C and 12D are views (print #7081) of an inner cup made of #304-SS for the device.

FIGS. 13A, 13B, 13C and 13D are views (print #7082) of an inner cup ring made of #304-SS for the device.

Figure 14:
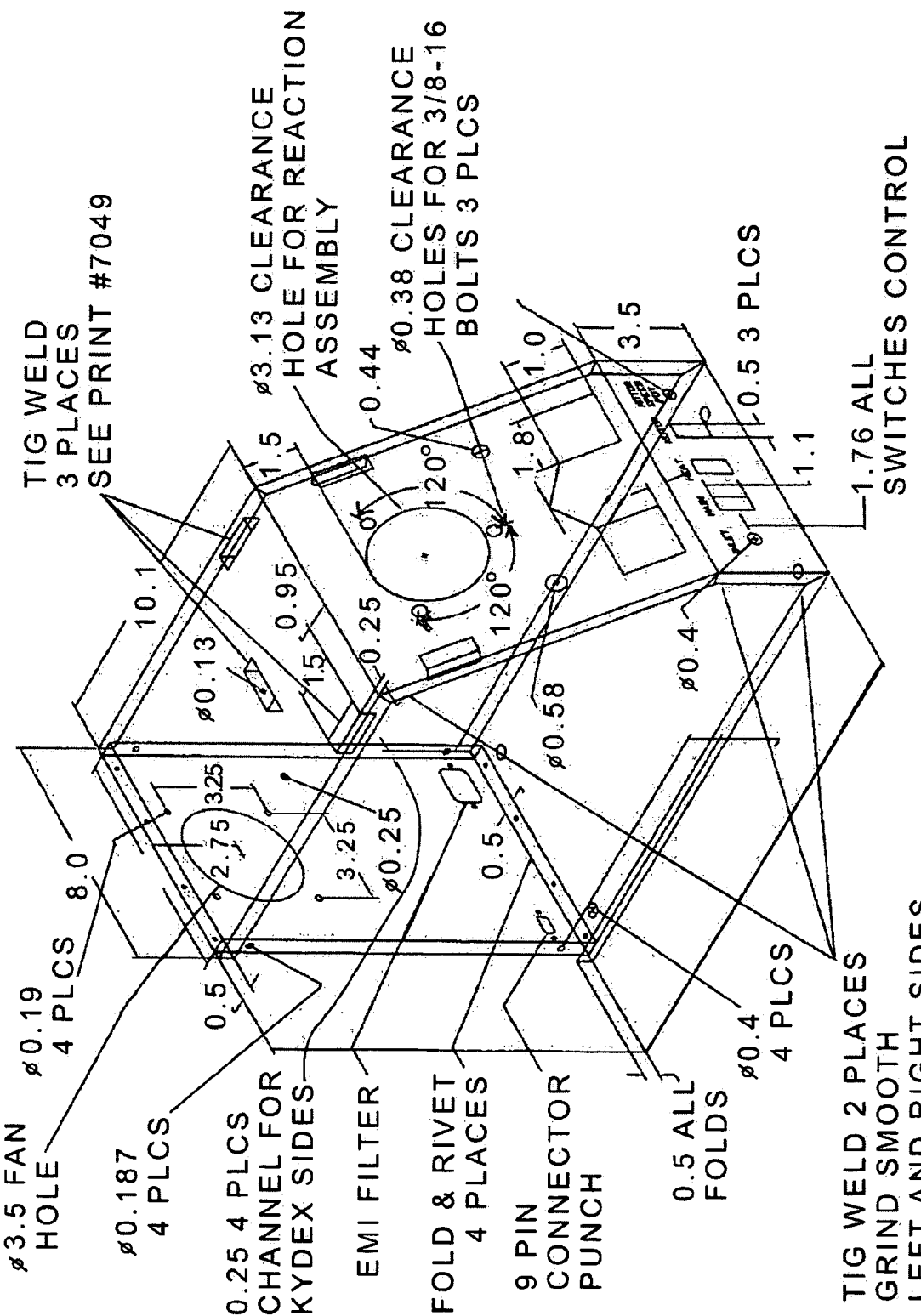

FIG. 14 is a perspective view (print #7083) of a cabinet made of 18-gage #304-SS sheet material for the device.

Figure 15A:
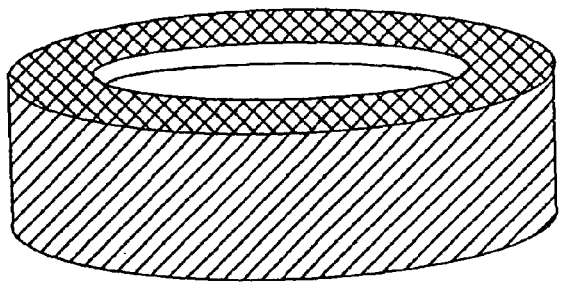
Figure 15B:
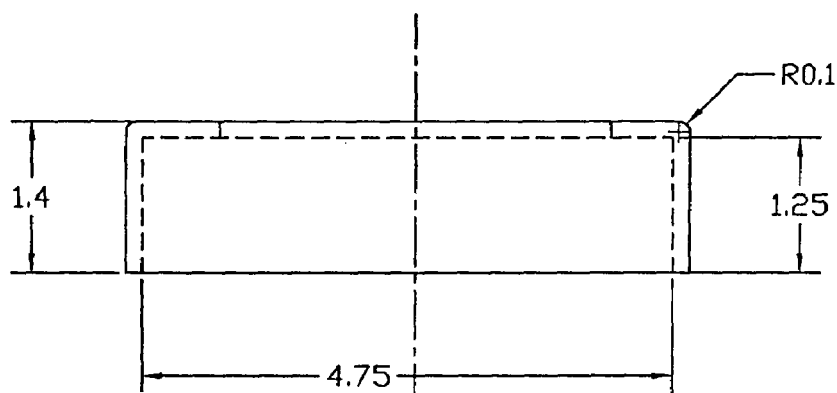
Figure 15C:
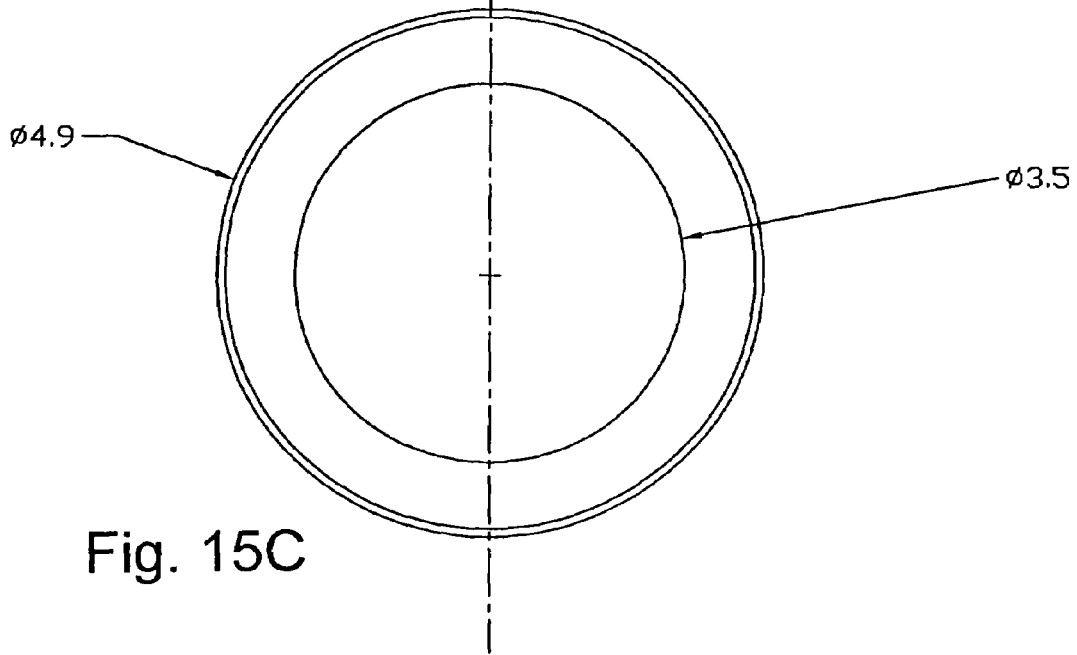

FIGS. 15A, 15B and 15C are views (print #7084) of a lid cover made of TEFLON polytetrafluoroethylene for the device.

Figure 16A:
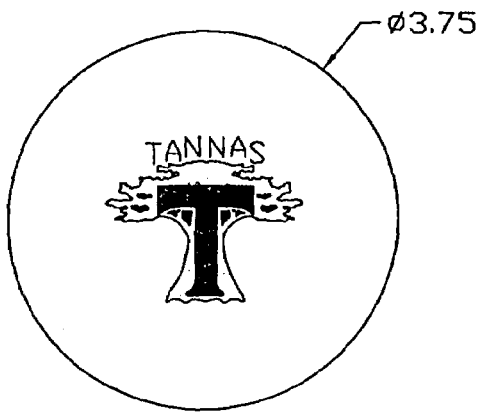
Figure 16B:
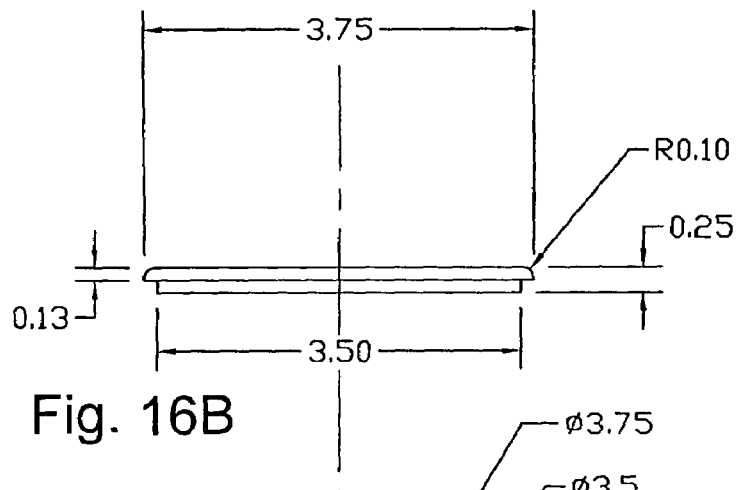
Figure 16C:
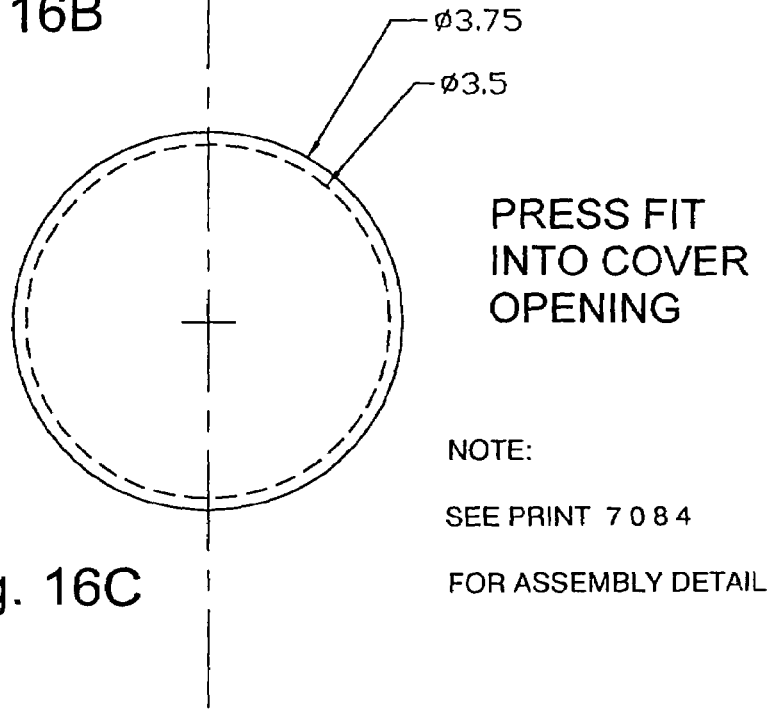

FIGS. 16A, 16B and 16C are views (print #7085) of a lid cover insert made for the TEFLON polytetrafluoroethylene lid cover of FIGS. 15A-C for the device.

FIGS. 17A, 17B and 17C are views (print #7086) of a pressure (bomb or reaction) lid made of #304-SS for the device.

Figures 18A, 18B:
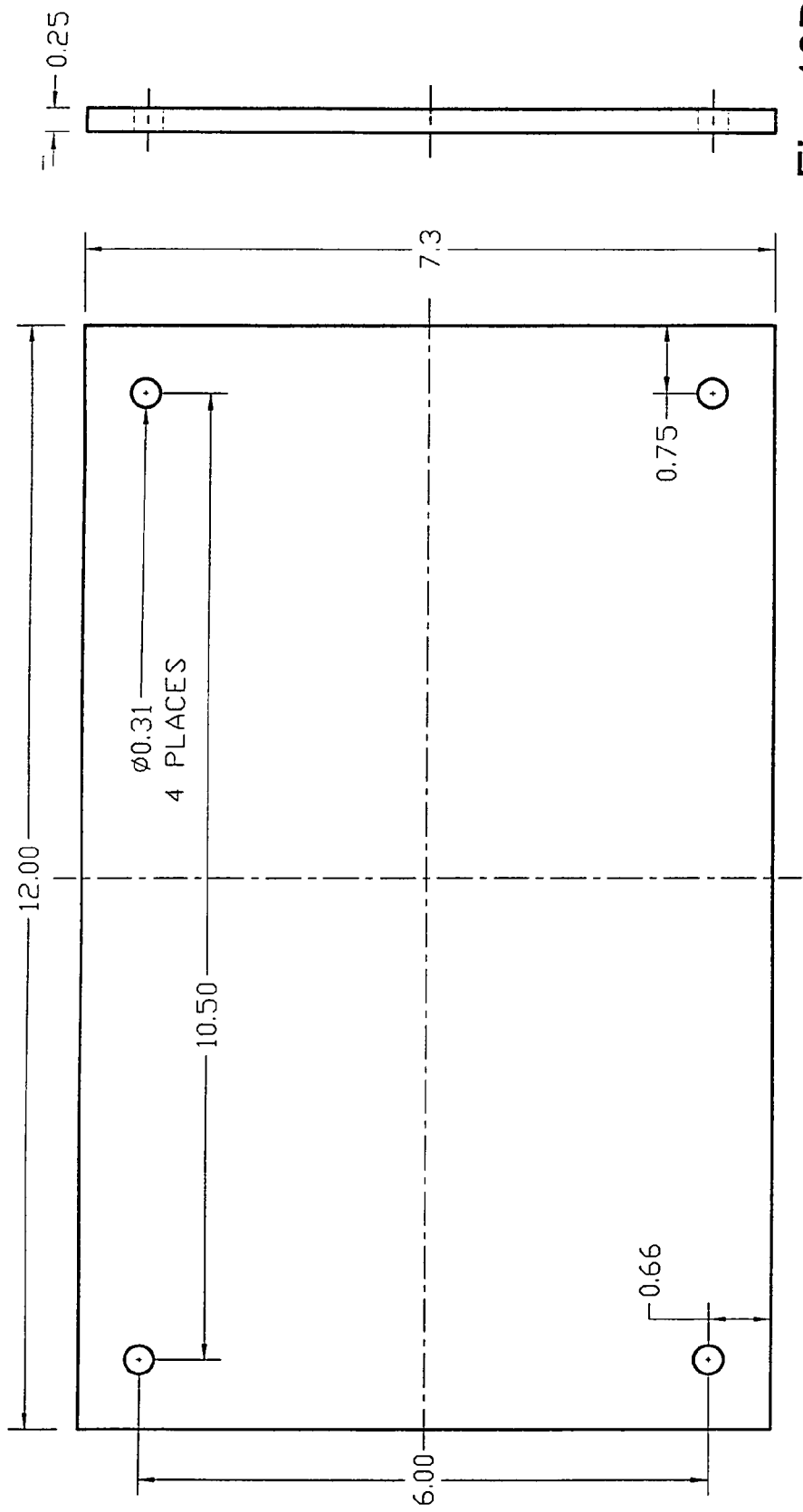

FIGS. 18A and 18B are views (print #7088) of a subplate of glass fiber reinforced insulating plastic (L-50) for the device.

FIGS. 19A, 19B, 19C and 19D are views (print #7089) of a cabinet back panel made of 18-gage #304-SS for the device.

FIGS. 20A and 20B are views (print #7090) of a cabinet component 30-degree datum made of #304-SS for the device.

Figure 21A:
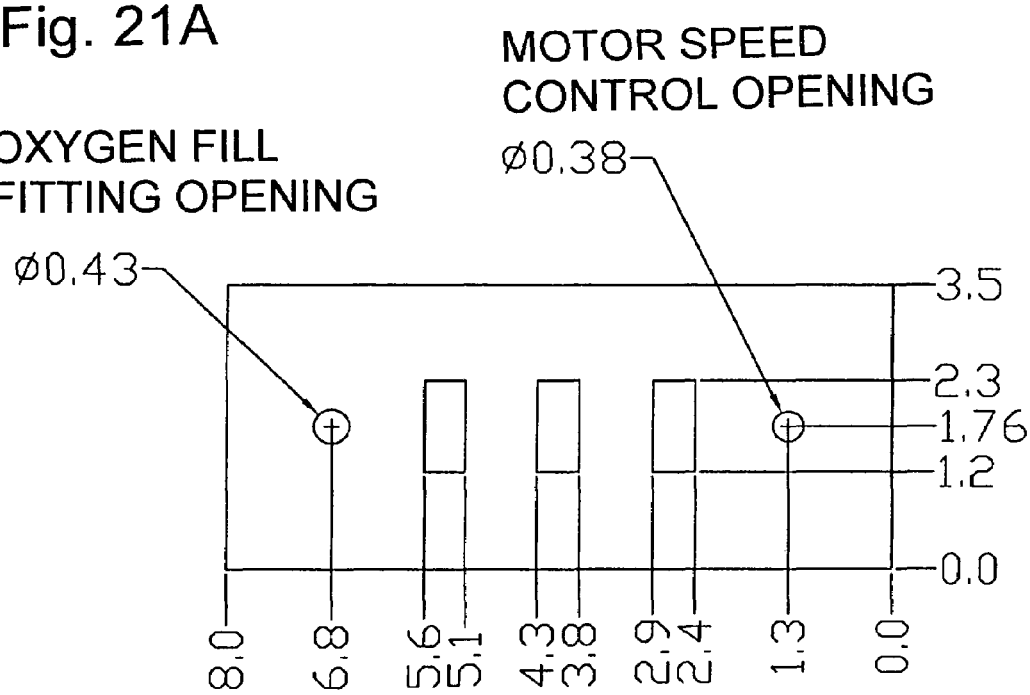
Figure 21B:
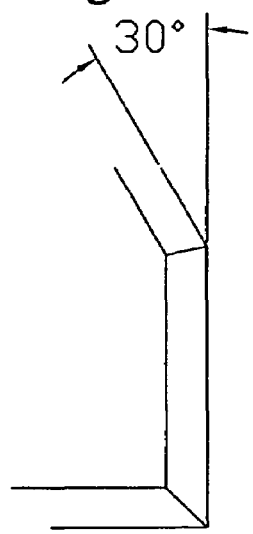

FIGS. 21A and 21B are views (print #7091) of a cabinet component lower front made of #304-SS for the device.

Figure 22A:
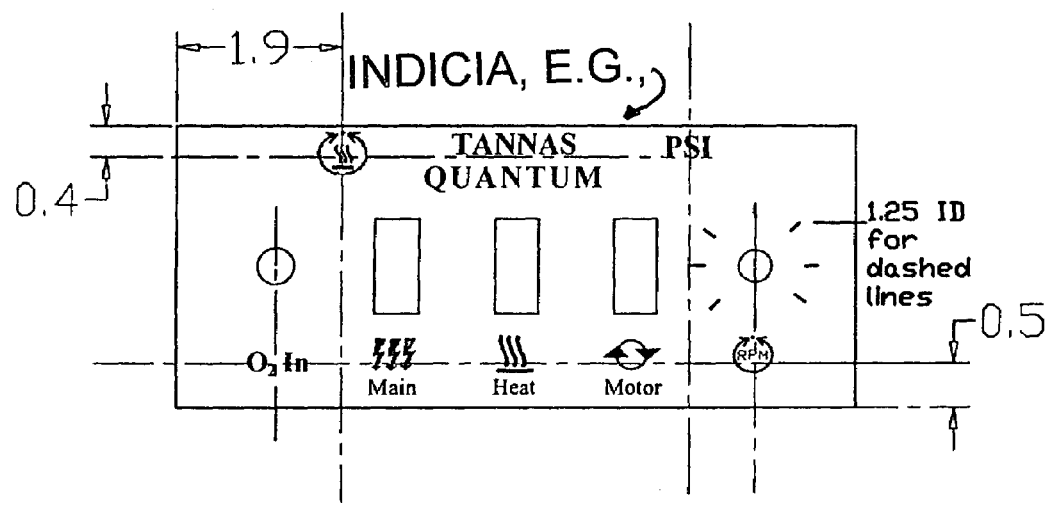
Figure 22B:
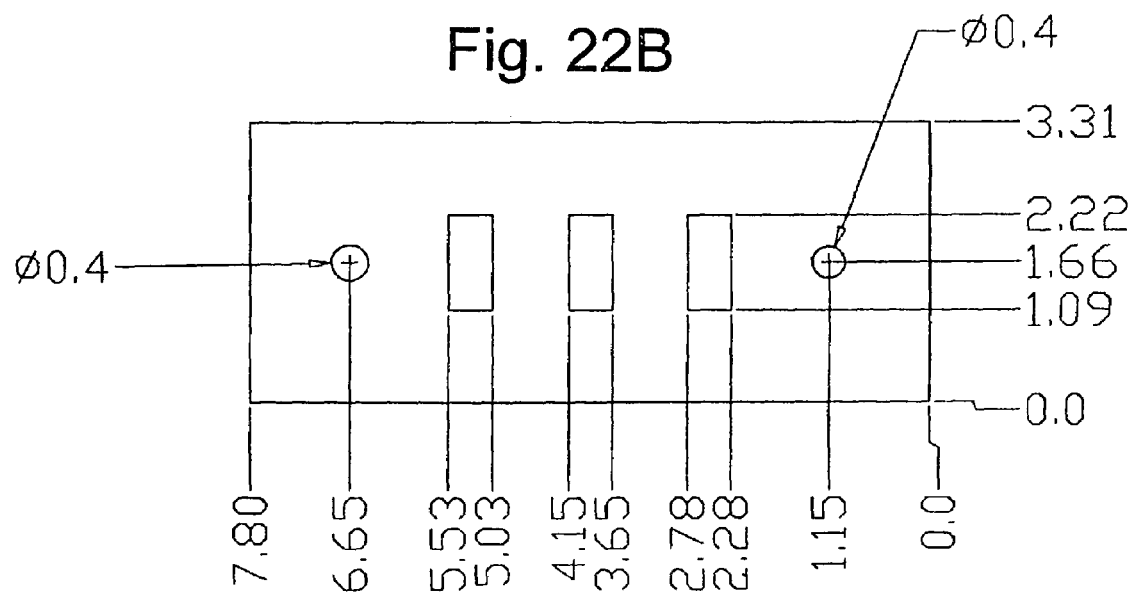

FIGS. 22A and 22B are views (print #7091-1) of illustrative cabinet component lower front labels on #304-SS for the device.

FIGS. 23A, 23B, 23C, 23D, 23E and 23F are views (print #7094) of a cabinet top panel made of 18-gage #304-SS for the device.

FIGS. 24A and 24B are views (print #7095) of a cabinet bottom made of 18-gage #304-SS for the device.

Figure 25A:
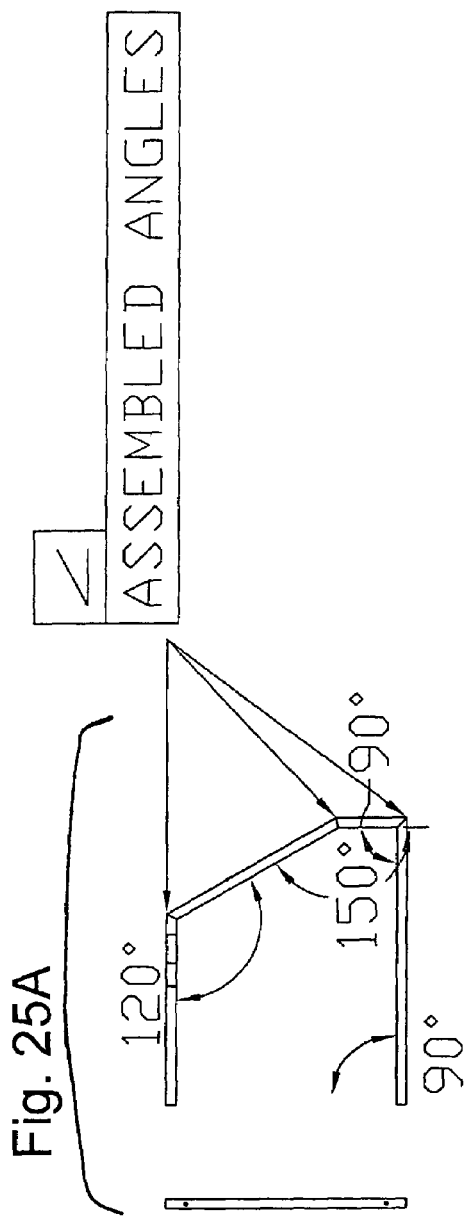
Figure 25B:
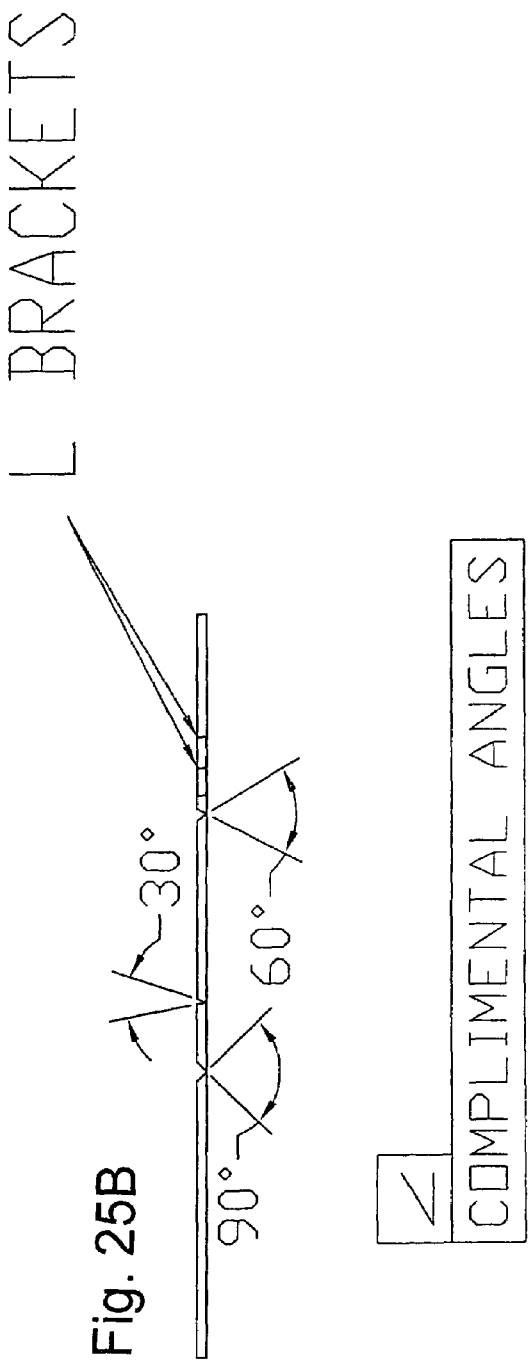

FIGS. 25A and 25B are views (print #7096) of cabinet angles, the cabinet made generally of #304-SS for the device.

Figure 26A:
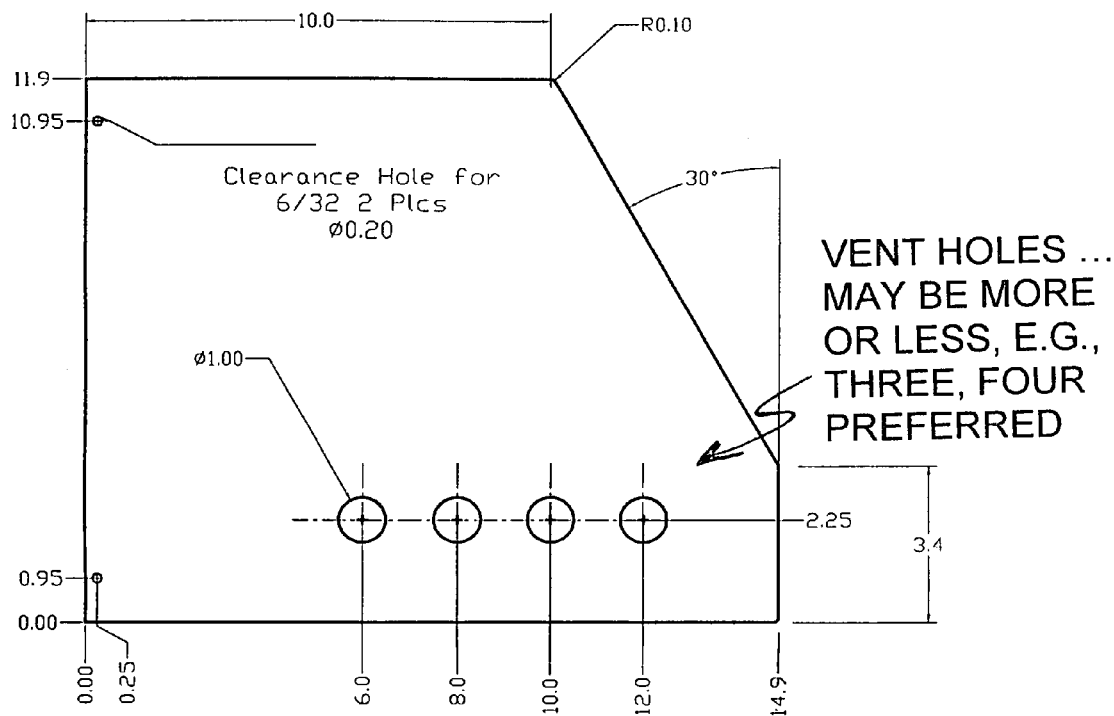
Figure 26B:
Figure 27C:
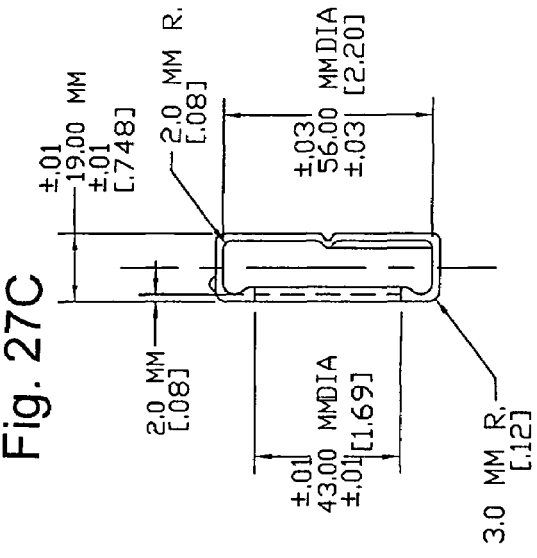
Figure 27D:
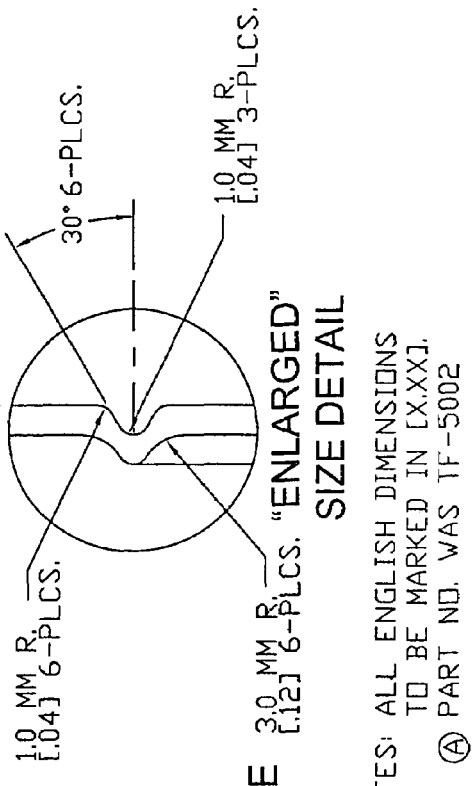
Figure 27A:
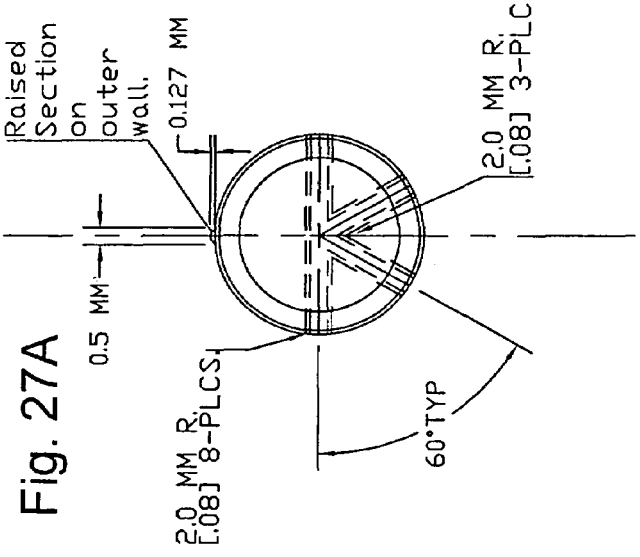
Figure 27B:
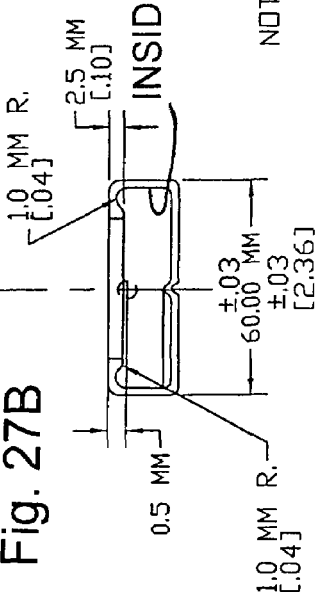

FIGS. 26A and 26B are views (print #7097) of cabinet side panels made of L-50 for the device.

FIGS. 27A, 27B, 27C and 27D are views (print #7098) of a reaction dish made of PYREX glass, notably for TFOUT type use, for the device.

FIGS. 28A, 28B and 28C are views (print #7100) of a bomb reaction cylinder made of #304-SS for the device.

FIGS. 29A, 29B, 29C and 29D are views (print #7101) of an inner cup bottom made of #304-SS for the device.

Figure 30:
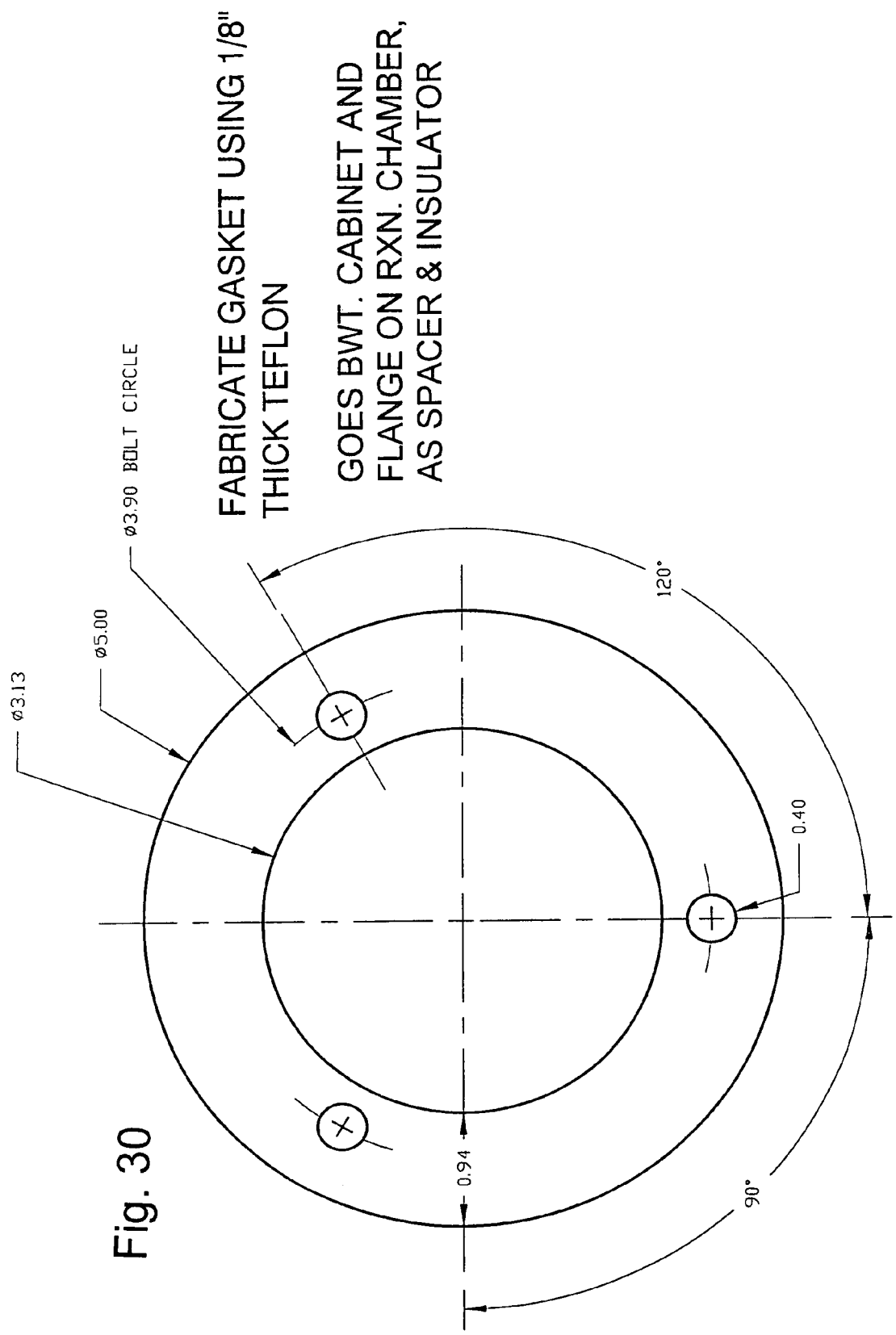

FIG. 30 is a view (print #7102) of a reactor gasket made of TEFLON polytetrafluoroethylene for the device.

FIGS. 31A, 31B and 31C are views (print #7103) of a reaction lid L-clamp made of #304-SS for the device.

FIGS. 32A, 32B, 32C, 32D, 32E and 32F are views (print #7104) of a motor coupling made of #316-SS for the device.

Figure 33:
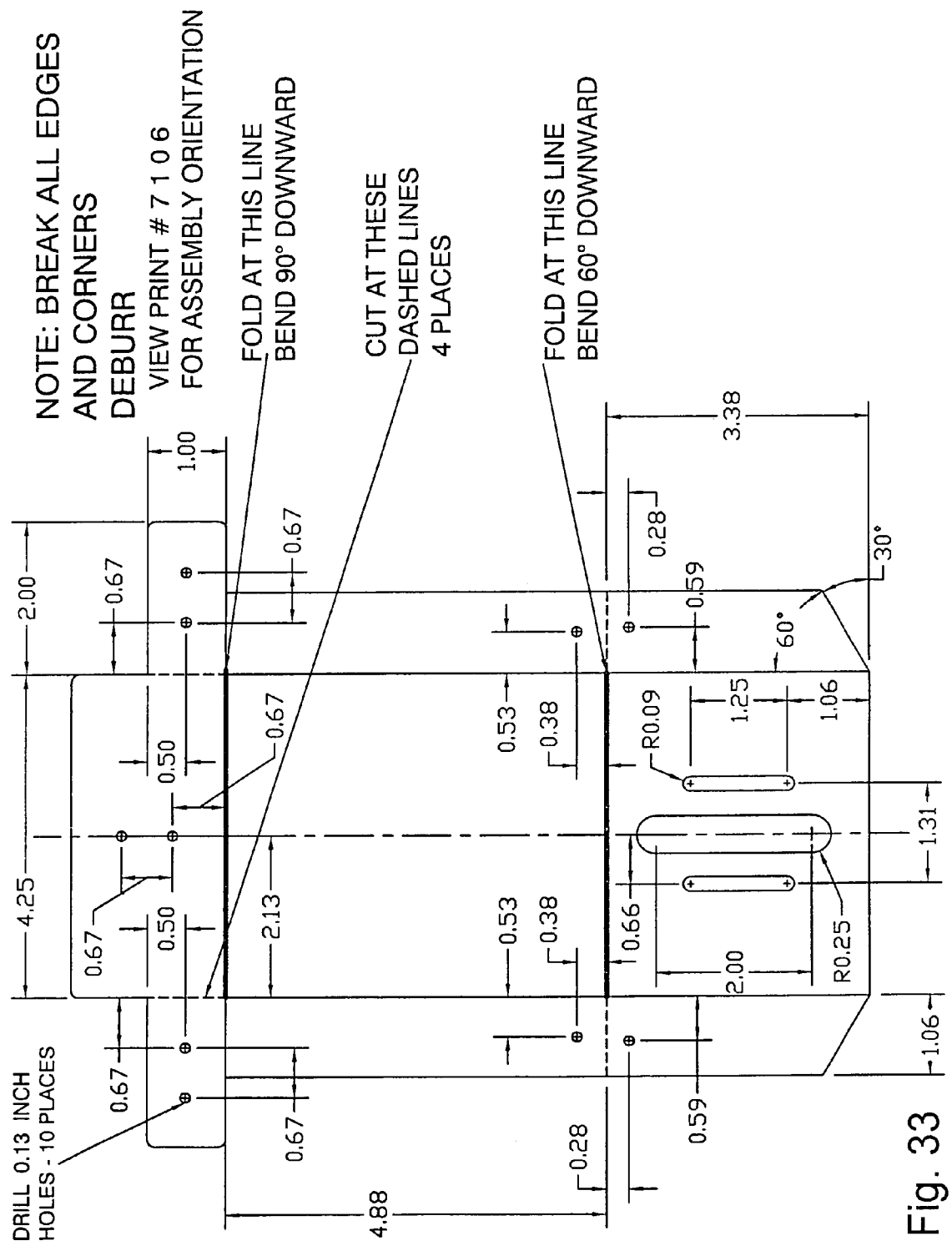

FIG. 33 is a view (print #7105) of a motor bracket, as yet flat, made of 1/16-inch steel for the device.

Figure 34:
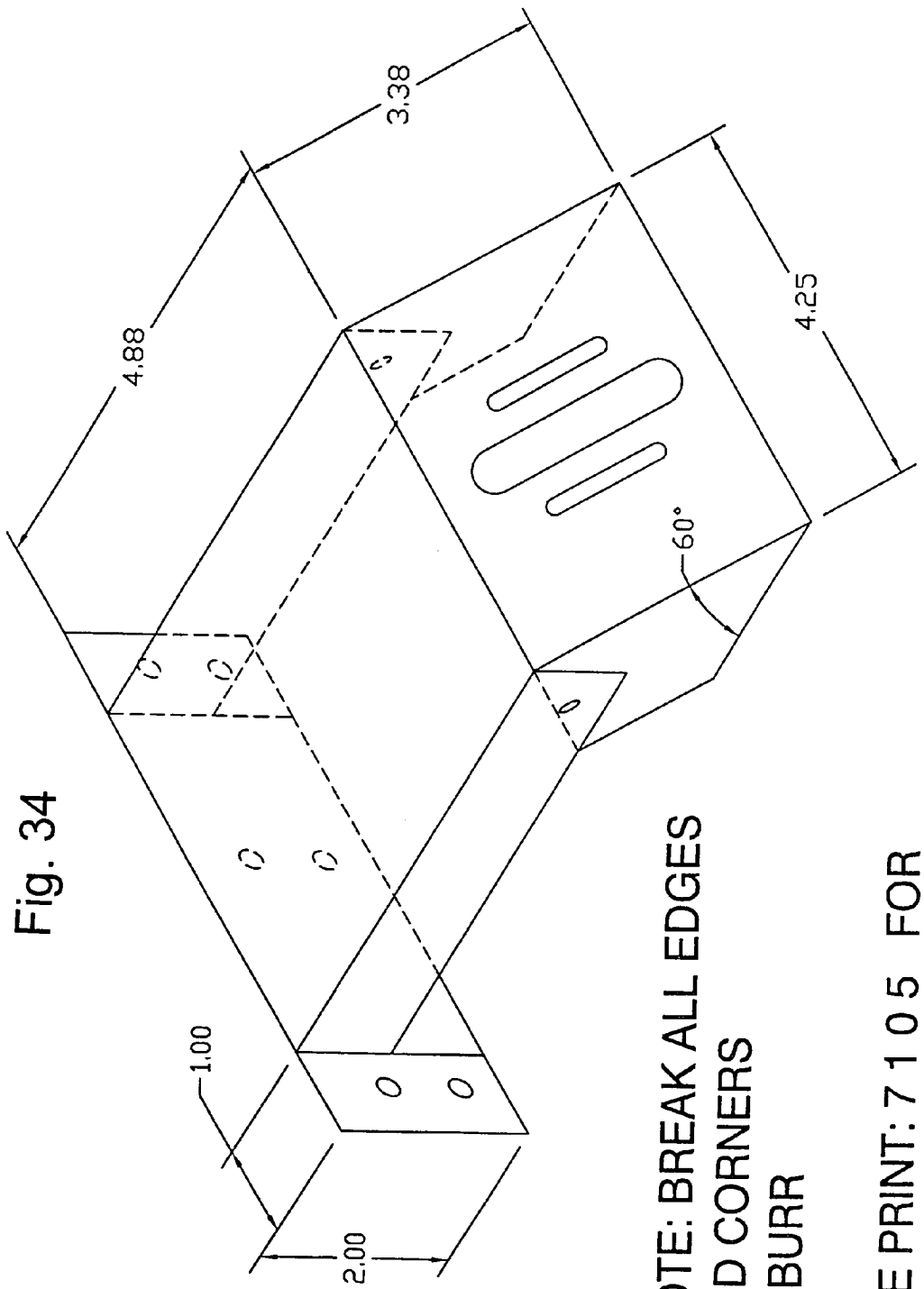

FIG. 34 is a view (print #7106) of the motor bracket assembly as formed into shape for the device.

FIGS. 35A and 35B are views (print #7108) of a magnet made with NED-35 steel plate for the device.

Figure 36B:
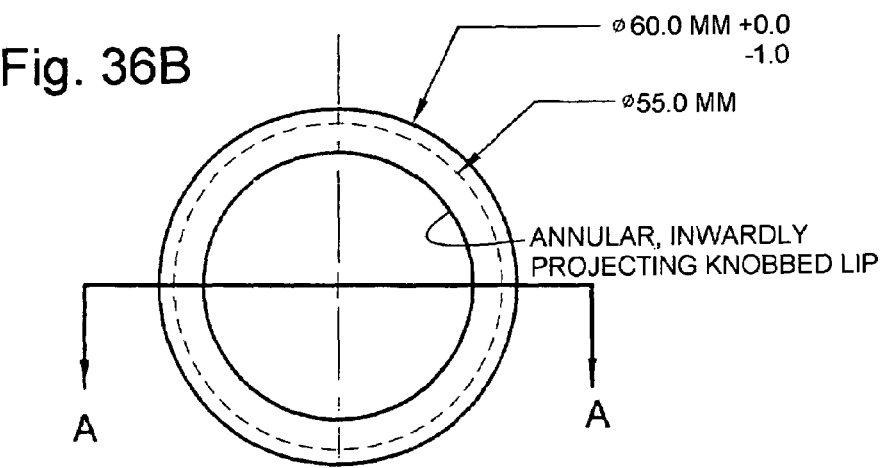
Figure 36A:
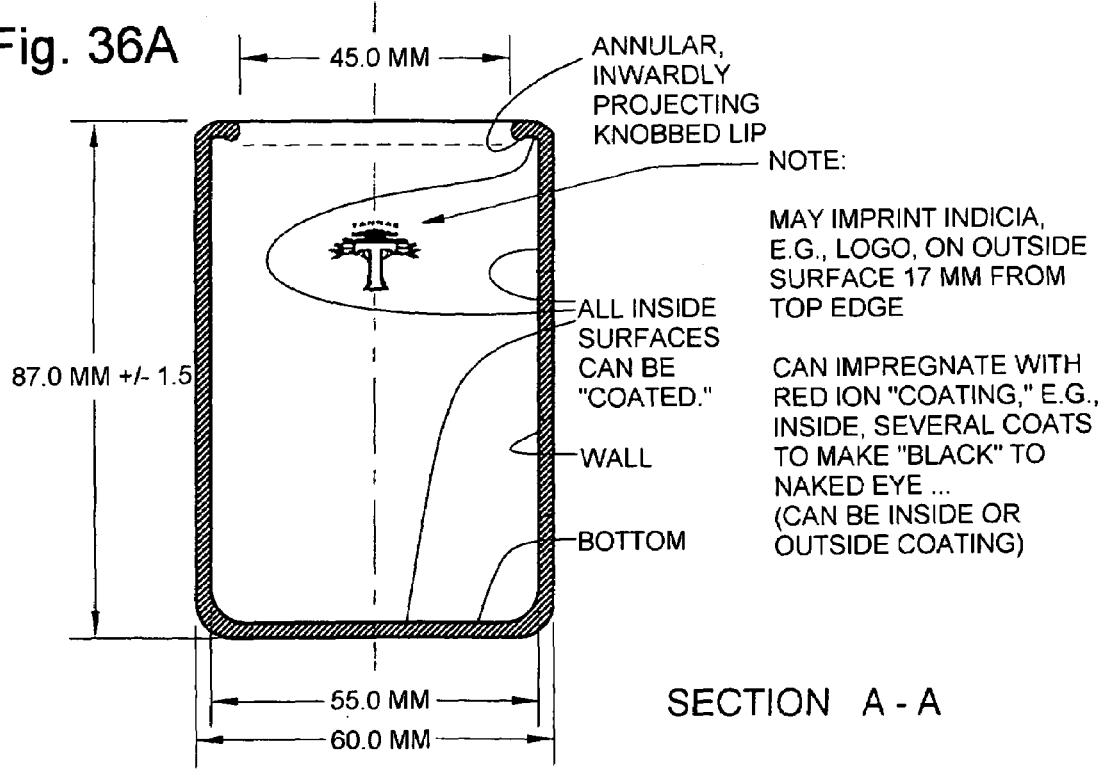

FIGS. 36A and 36B are views (print #7109) of sample flask of borosilicate glass, including for RBOT type use, for the device.

FIGS. 37A, 37B, 37C and 37D are views (print #7110) of a cup assembly made of #316-SS for the device.

Figure 38:
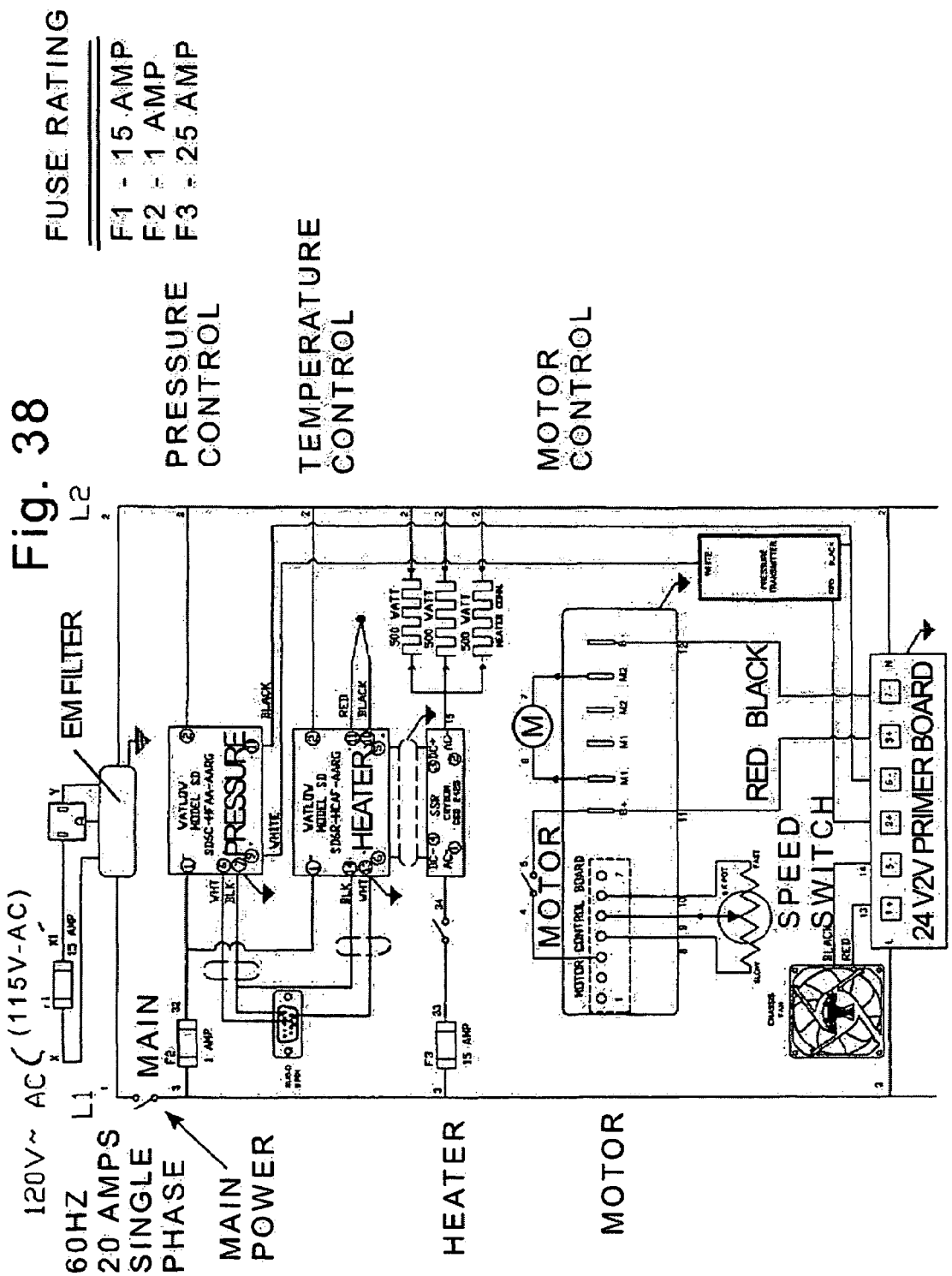

FIG. 38 is a view (print #7107) of a ladder/circuit diagram for the device.

Figure 39:

FIG. 39 is a left front view of the device of FIG. 6.

Figure 40:
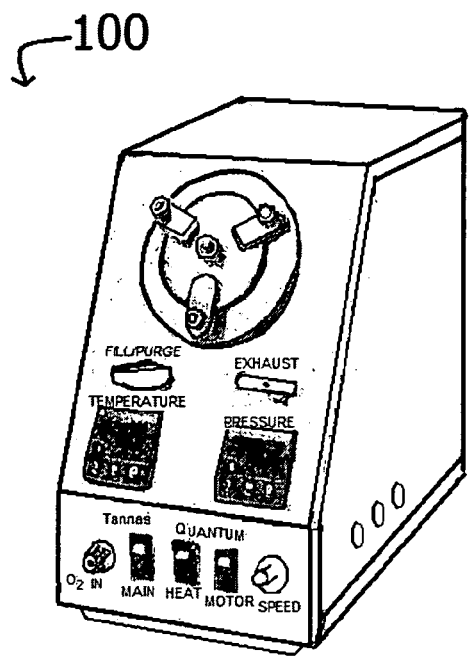

FIG. 40 is a right front view of the device of FIG. 6.

Figure 41:
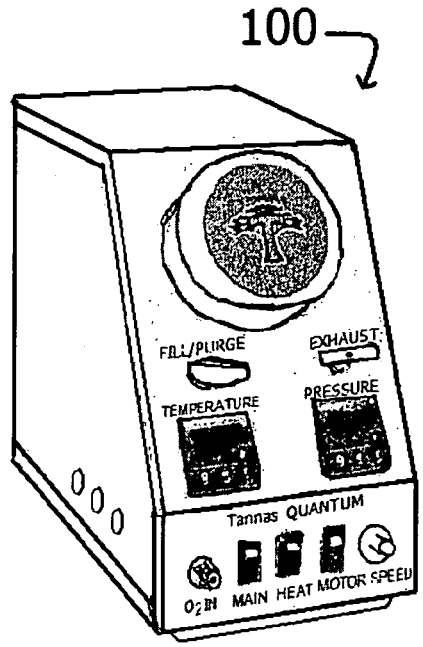

FIG. 41 is a left front view of the device of FIG. 6 with lid cover installed.

Figure 42:
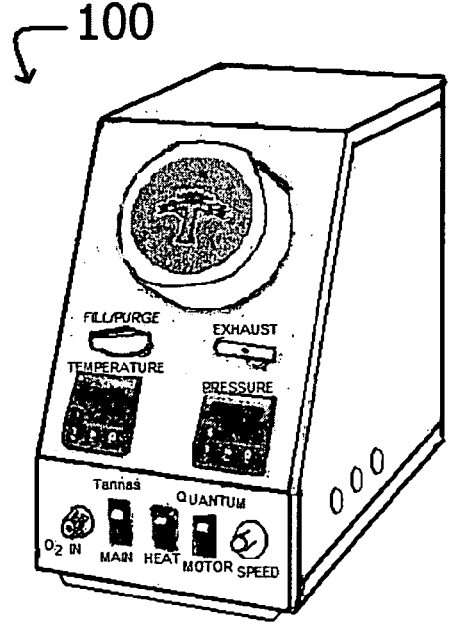

FIG. 42 is a right front view of the device of FIG. 6 with lid cover installed.

Figure 43:
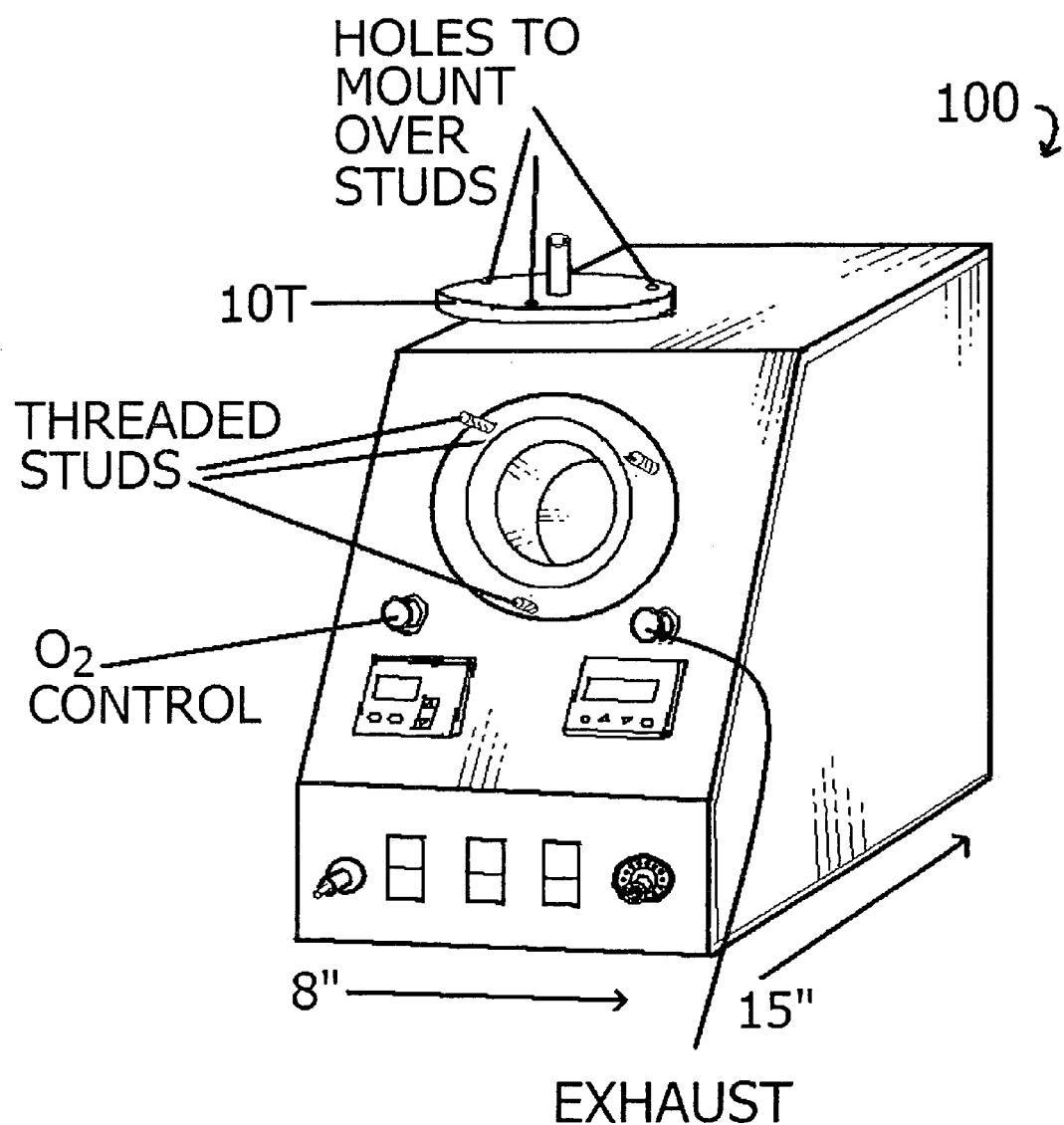

FIG. 43 is a right front view of another embodiment of the device of the invention, including a screw-down lid, which is resting on the top of its cabinet. Compare, FIGS. 2 and 3.

Figure 44:
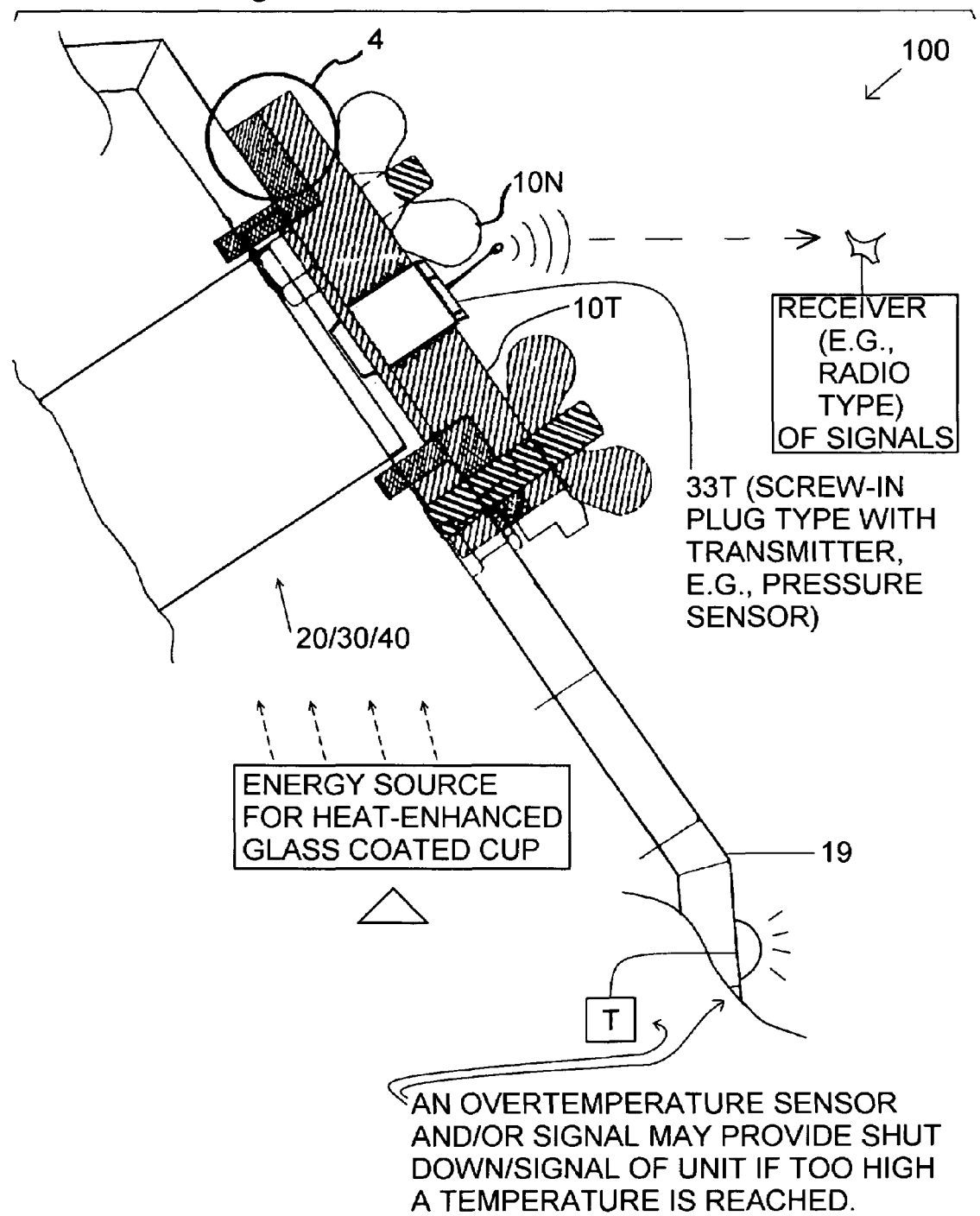

FIG. 44 is a plan view of another embodiment of the device of the invention, having a contrivance for wireless communication of a bomb property.

Figure 45:
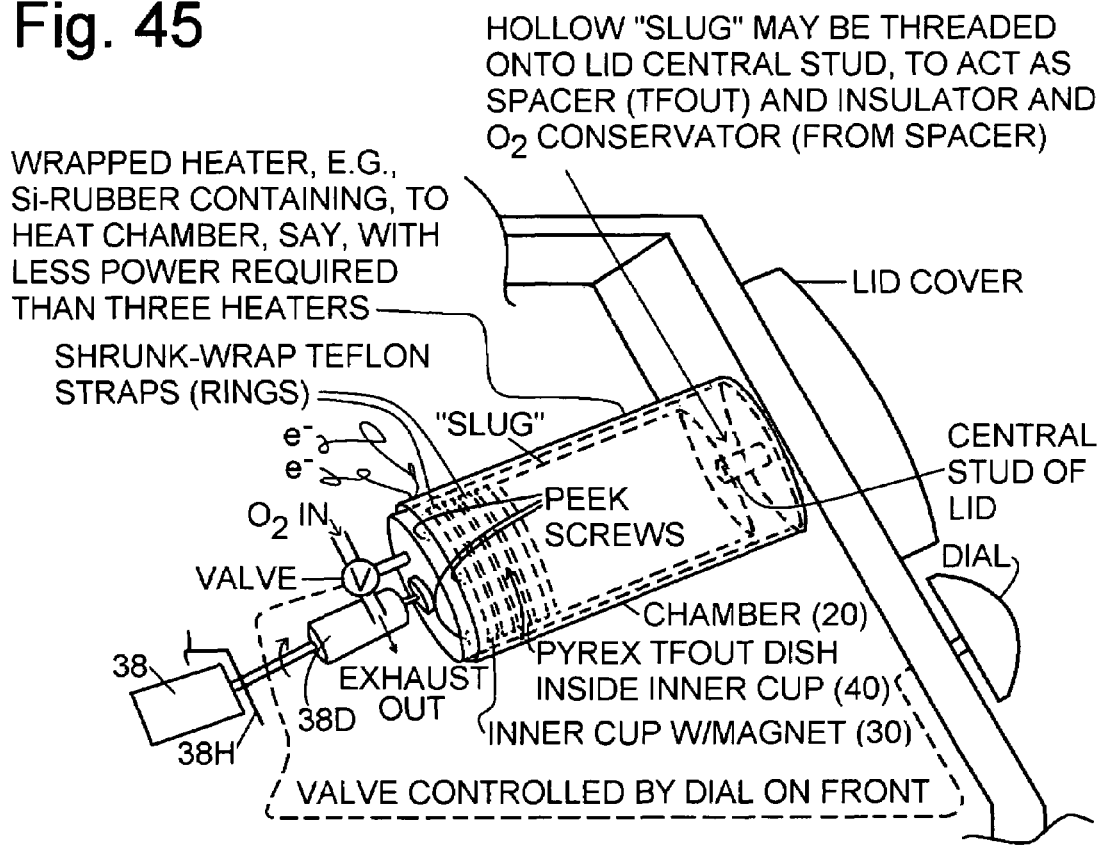

FIG. 45 is a side plan view of another embodiment of the device of the invention, in part, having an oxygen-pressure entry and exhaust gas exit controlled by a valve in a T-stem, and a single wrapped electric heater. This is illustrated as configured for TFOUT testing.

Figure 46:
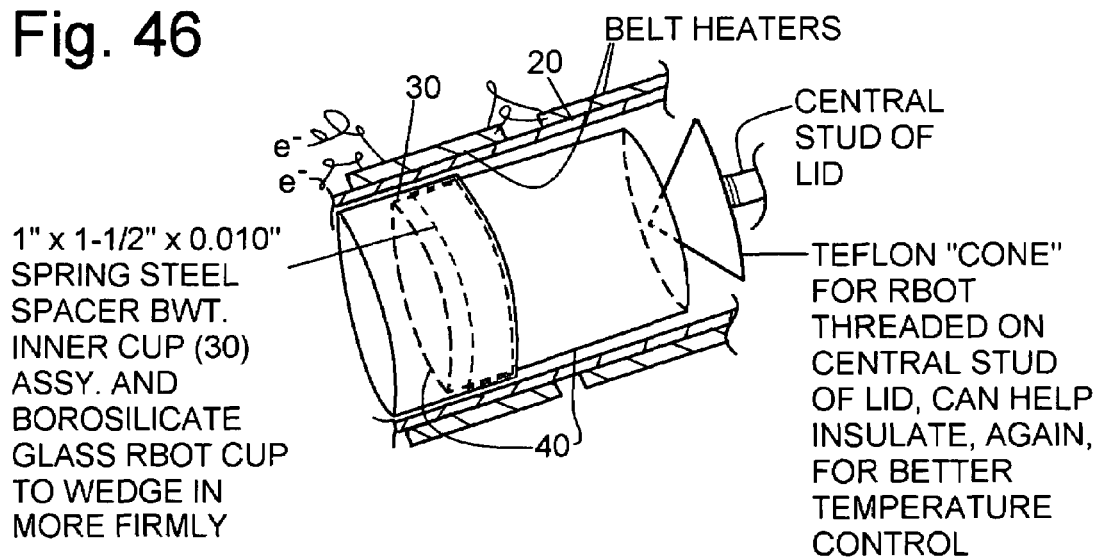

FIG. 46 is a side plan view of an embodiment of pertinent parts of the device of the invention, illustrated as configured for RBOT testing.

FURTHER DETAIL ILLUSTRATIVE OF THE INVENTION

The invention can be further understood by the detail set forth below. The same, as in the case with the foregoing, is to be taken in an illustrative and not necessarily limiting sense.

With respect to the drawings, although many configurations are possible, in general, rotatable bomb device 100 includes housing 10, support 20 for a rotatable component to a vessel, and the rotatable component 30 to the vessel. Rotating vessel 40 may be provided thereby/therewith. Other components may be provided.

The housing 10 may be made, for example, of two basic parts, lower cradle 11 and upper cap 12 (FIG. 1), for instance, made of any suitable metal, for example, aluminum, which has rotatable bomb arm opening 13. Hollow interior 14 is provided. Insulation 15 may be provided around or as part of the housing 10. One or more heaters 16 are typically provided for reactions and tests such as rod or bullet electrical resistance heaters (FIG. 1) or belt heaters (FIGS. 2, 3, 9, 10), say, two, each with 400-watt capacity, or, say, three each, which may be regulated with a 110~220-volt solid state relay (SSR), or a silicone rubber type wrap-around heater (FIG. 45). Heat may be monitored by one or more thermocouples 17. The housing 10 may beneficially sit in an angled position, and may be supported by housing support 18, made, for example, of plastic, which may be a non-foamed or foamed structural resin, metal, wood or any other suitable material, and/or outside support cabinet 19, made, say, of sheet metal, for example, of stainless steel, and/or suitably strong plastic, for example, KYDEX plastic, which may be backed with metal sheeting to provide an electronic guard. A surrounding stationary unit that provides a bomb may be considered to be the housing 10, which may be attached to the outside support cabinet 19 and/or other feature(s) inside the cabinet 19, and such a unit can include cup 10C, sealing gasket 10G, preferably L-clamps 10L, sealing nuts 10N, and top 10T, into which the vessel 40, which may be open, say, in the form of another cup (reaction vessel or reaction cup) such as made from glass. The latter arrangement, in consideration of a heating element such as the belt heaters 21, may be considered an outer heating chamber. Feature(s) such as knurling, or one or more cooperative ridges and grooves, for example, in a circular or a concentric pattern, may be provided in such a unit to assist in securing any gasket 10G under high pressure testing and/or reaction.

Figure 1:
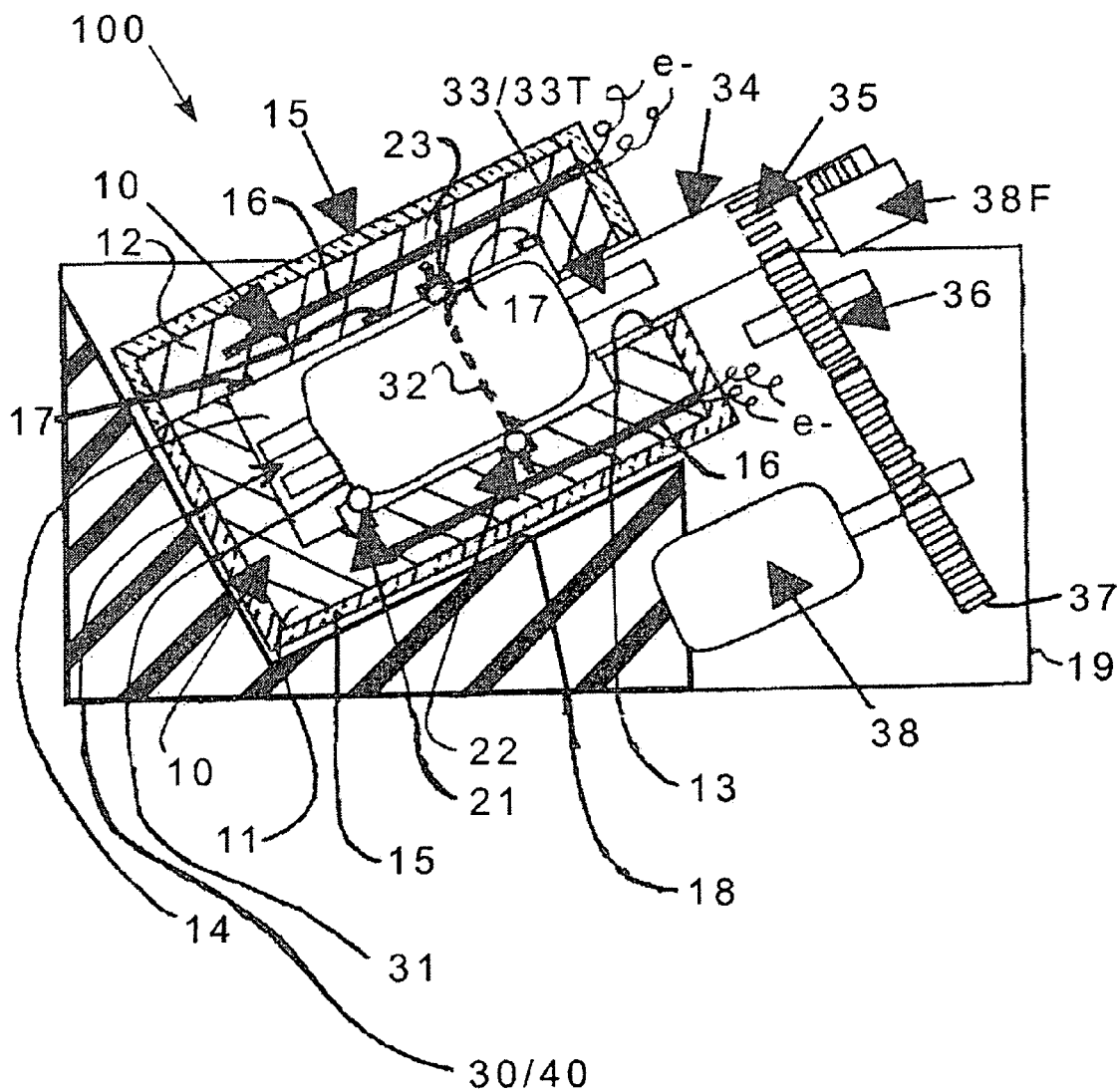
FIG. 1 shows a side plan view in partial section of a rotatable bomb device of the invention, which is rotated through mechanical gears.

As for the support 20, this may be bearing surface 20, say of the reaction chamber, although many types and configurations are possible, which may range from simple, smooth gliding surfaces to needle or ball bearings, to air or liquid surround or flotation. Lower ball bearing 21 and middle ball bearing 22 may be provided on a lower portion of the housing 10 (FIG. 1) where the lower bearing 21 serves as a stop and friction-ameliorating surface for a large vessel 30 with the middle bearing 22 serving an auxiliary bearing function, or, for a smaller vessel 30, the middle bearing 22 can serve as a stop and friction-ameliorating surface. Other bearings may be provided in the housing 10, as an example, upper middle bearing 23 may be provided (FIG. 1). Bearings may be supported by bearing stands such as is the bearing 21, or may be urged from the housing a suitable distance in bearing housings by springs as may be the bearings 22, 23 (FIG. 1). Bearing(s) 21, say, which may be mechanical bearings such as ball or needle bearings or of any other suitable variety, for instance, TEFLON polytetrafluoroethylene or TEFLON-coated surface(s), may be provided in predetermined position(s), say, a lower position, in the same location for multiple testing configurations, and these may assist in stabilizing an internal motive drive as well as the rotating component 30 together or, say, by affixing the component 30 to the internal motive drive that may have such bearing support such as small, solid TEFLON-coated surface or point contact 24 providing support in another position (FIGS. 2, 3).

As for the rotating component 30, it can be a hollow bomb, an open canister, or other container made of any suitable material such as an appropriate metal, plastic, ceramic or glass, for example, a suitable stainless steel that may or may not be magnetic, or high-temperature glass. The component 30 may be provided in any suitable shape or size. The component 30 may form the bomb (FIG. 1). Beneficially, especially when the device 100 is adapted for oxidization testing of oleaginous fluids, it is provided in one form 31 as alluded to above that has a larger sample vessel (FIGS. 1, 2), say, of a shape and size suitable for ASTM-D-2272 testing and the like, and another form 32 as alluded to above also that has a smaller sample vessel (FIGS. 1, 3), say, of a shape and size suitable for ASTM-D-4742 testing and the like. In the latter case, a spacer 32S, say of a wood, metal or plastic, advantageously of or coated with TEFLON plastic, may advantageously be provided (FIG. 3). As an oxidative uptake test device, the device 100 can include gas monitoring system 33, which may include oxygen supply 33S and/or gas pressure tap and/or transducer 33T (FIGS. 1-3), which may signal in a wireless manner, say, by radio (FIG. 44). Provided also can be epoxy or hard insulator sleeve 34 (arm), inset cogs 35 for receiving teeth of rotating idler gear 36 that is turned by motor gear 37 attached to the rotor of motor 38, and finger box 38F can be provided for controlling the rotating container 30 manually, for example, during set up or clean up (FIG. 1). The motor 38 may include magnet driver 38D, be connected to the housing 10 by housing mount 38H, and may turn magnet 38M, which may be mounted to the container 30 by screws 38S that secure intermediate, low-friction washer bushings 38W, say, which are of TEFLON plastic or TEFLON-coated, which can also contact an inner wall of the housing 10 and provide the support 20, 21 (FIGS. 2, 3).

Figure 2:
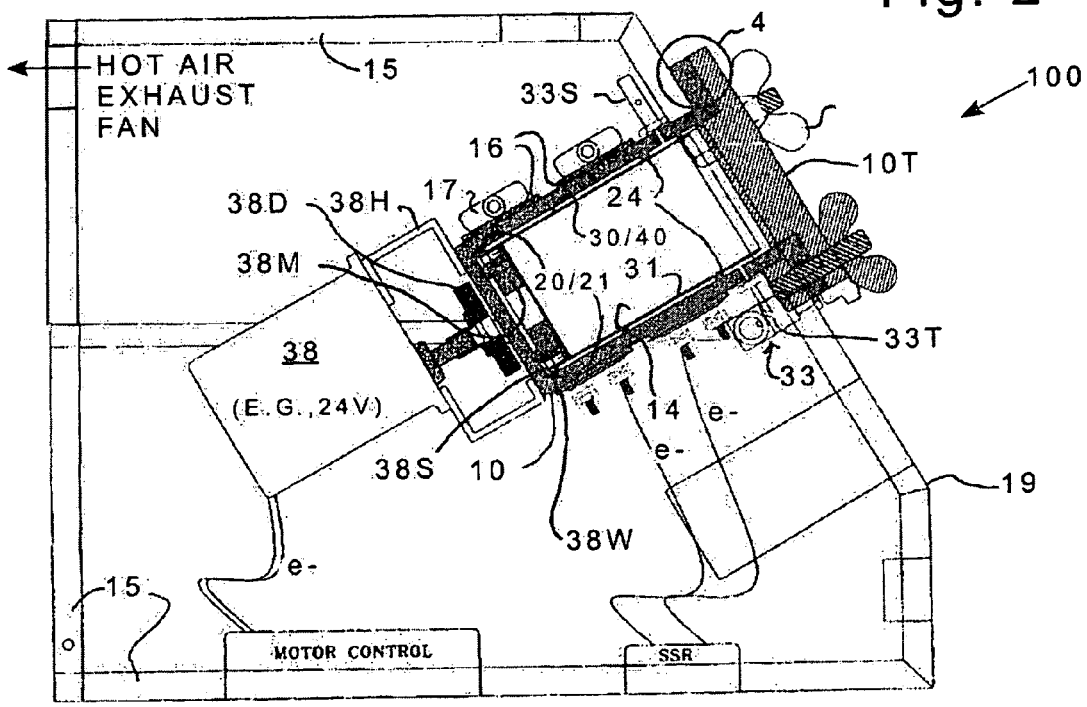
FIG. 2 shows a side plan view in part section of a rotatable bomb device of the invention, which is rotated through magnetic force, in a first configuration for ASTM D-2272 testing.
Figure 3:
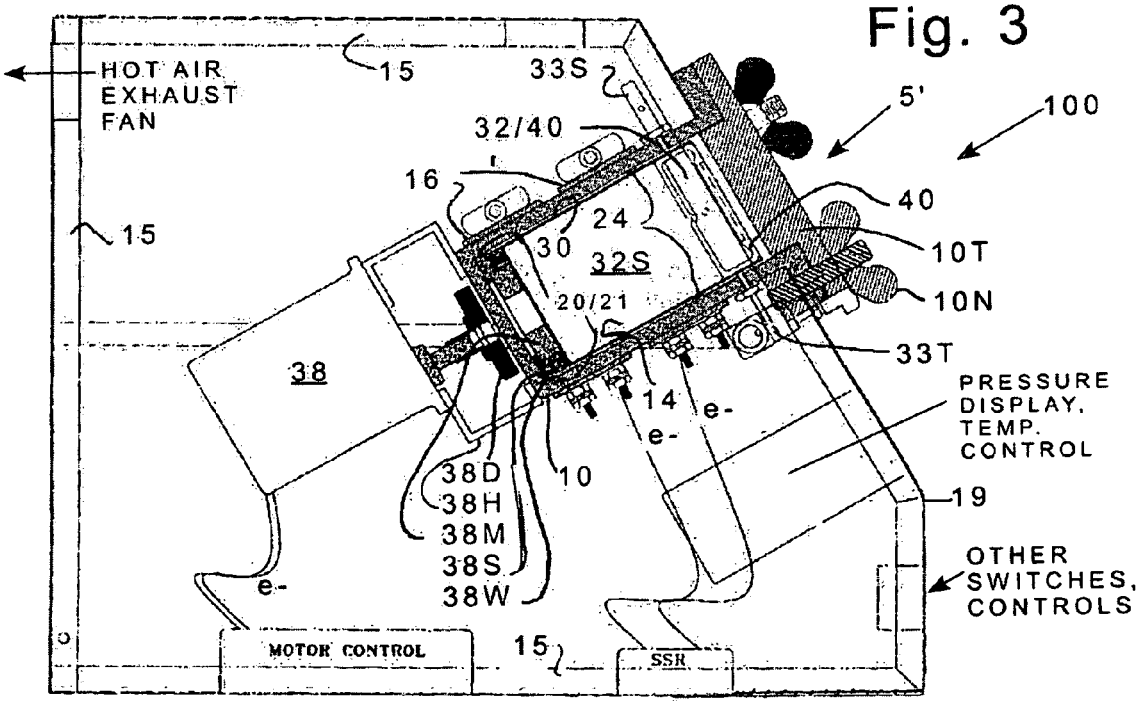
FIG. 3 shows a side plan view in part section of the device of FIG. 2, in a second configuration for ASTM D-4742 testing.
Figure 4:
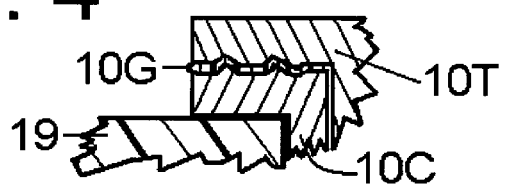
FIG. 4 is a detailed sectional view of part of the device, taken within the circle 4 found in FIG. 2.
Figure 5:
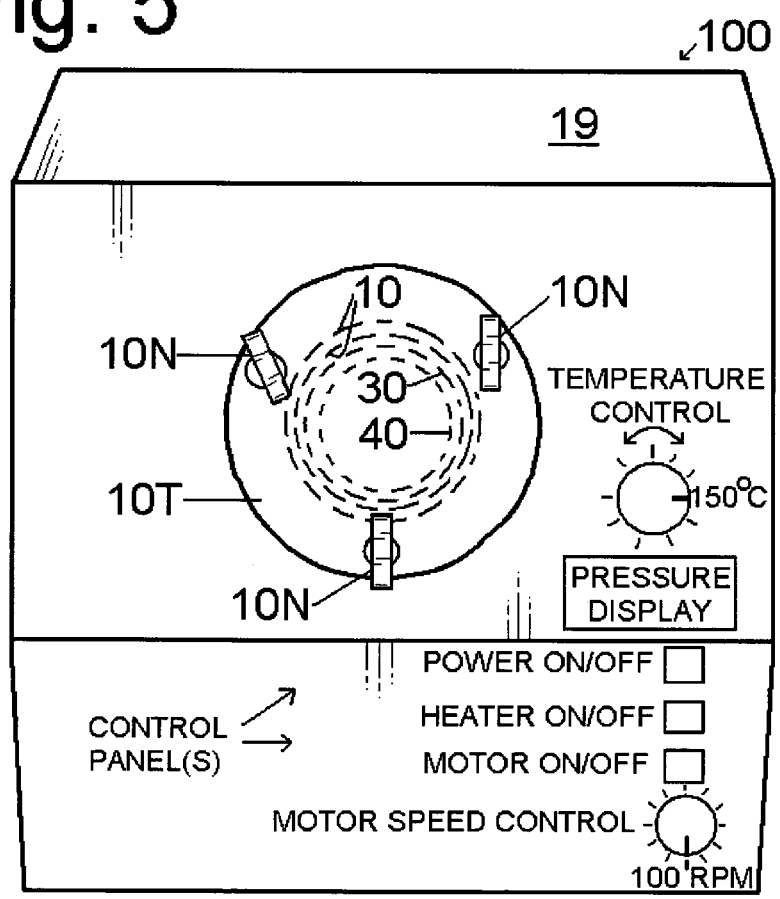
FIG. 5 is a front view of the device, taken along arrow 5 found in FIG. 3.
Figure 7:
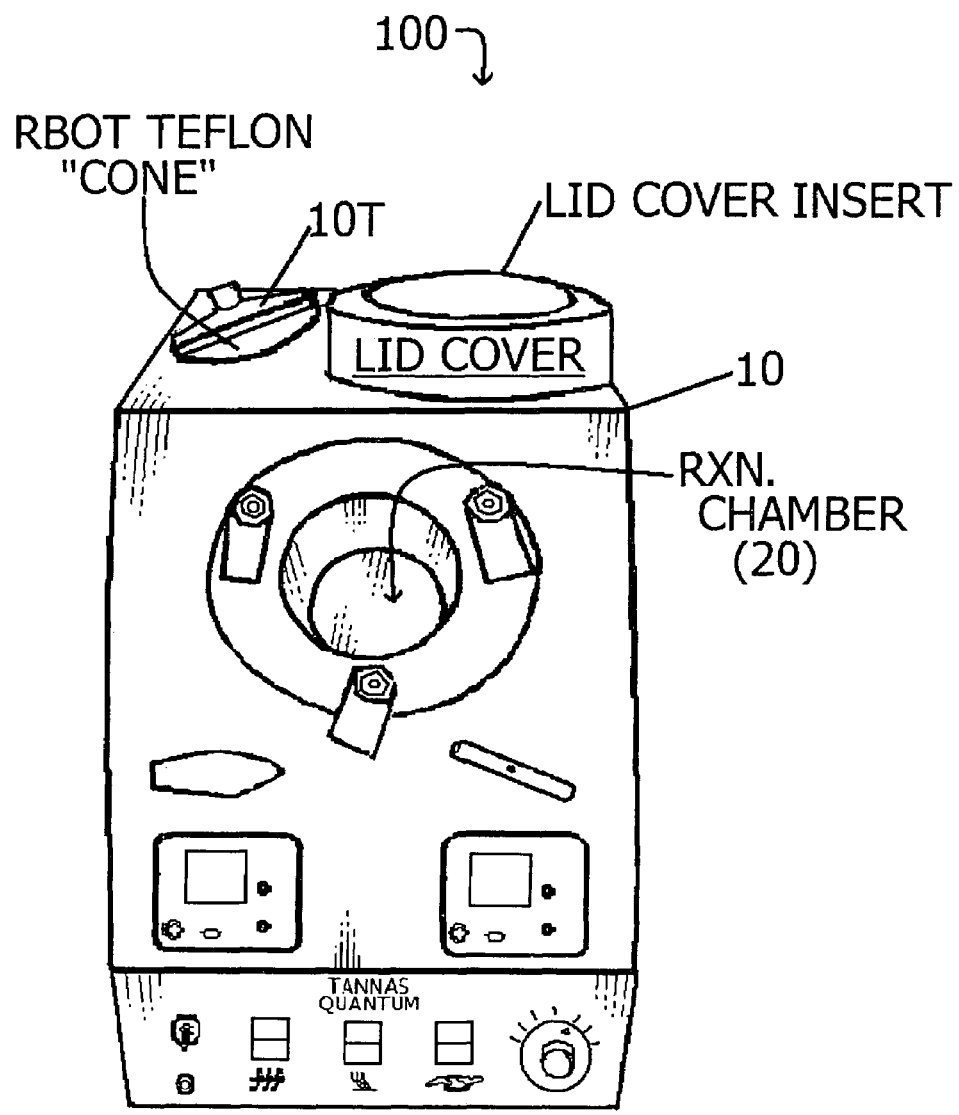
FIG. 7 is a front view of the device of FIG. 6, with its bomb chamber opened and its removed lid and lid cover resting on top of the cabinet of the device.
Figure 8:
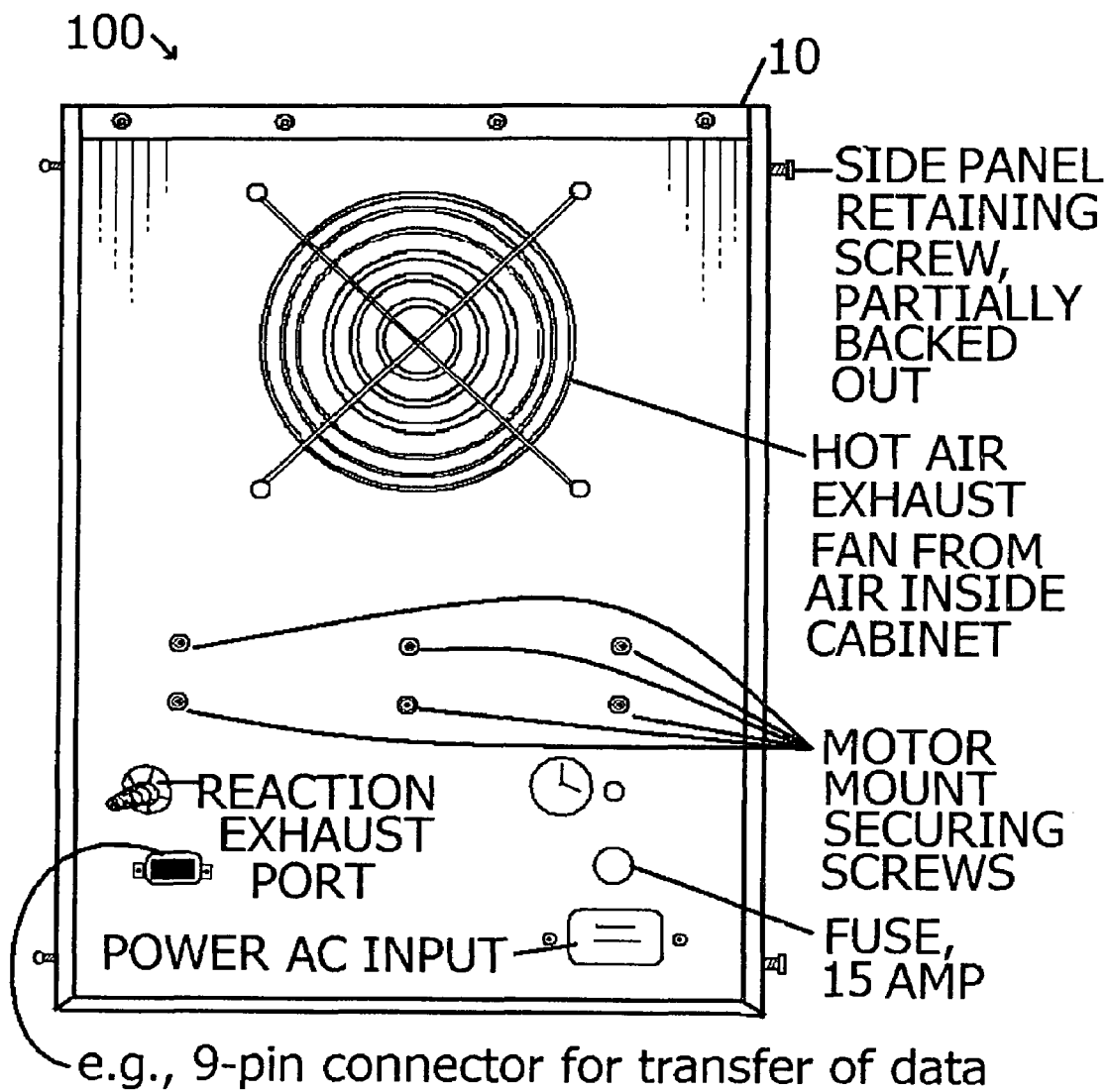
FIG. 8 is a rear view of the device of FIG. 6.
Figure 9:
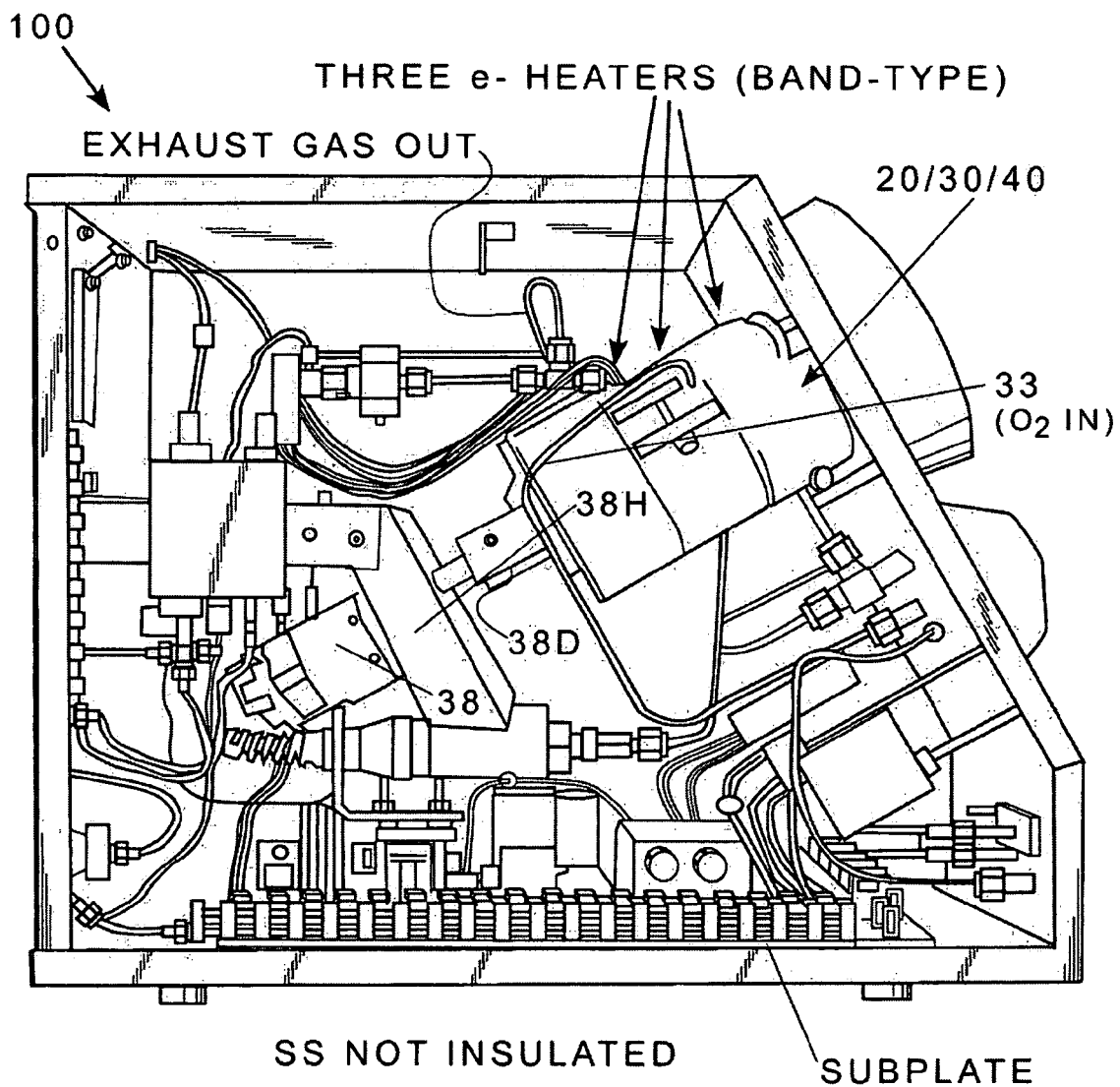
FIG. 9 is a left side view of the device of FIG. 6, with its left hand side panel removed for viewing internal components.
Figure 10:
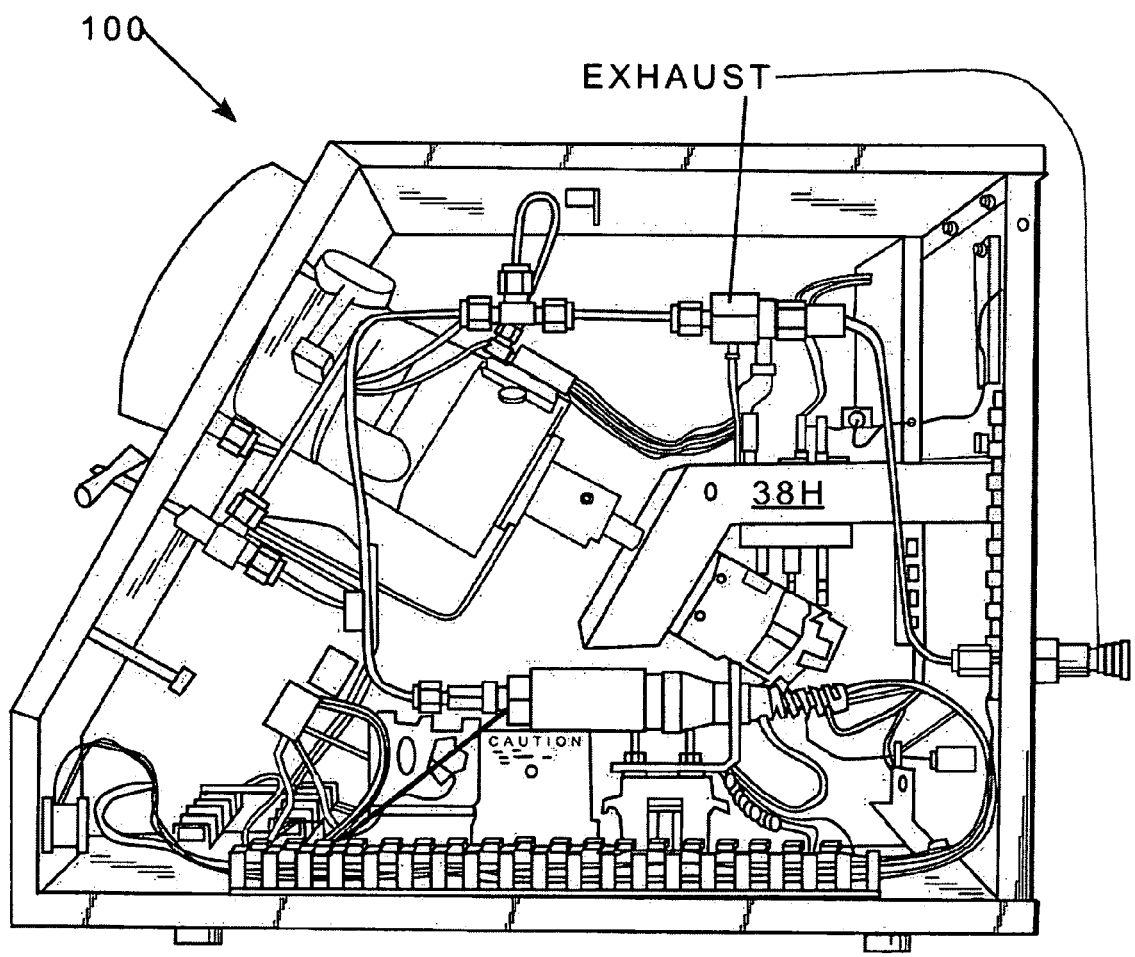
FIG. 10 is a right side view of the device of FIG. 6, with its right hand side panel removed to view internal components.
Figure 11:
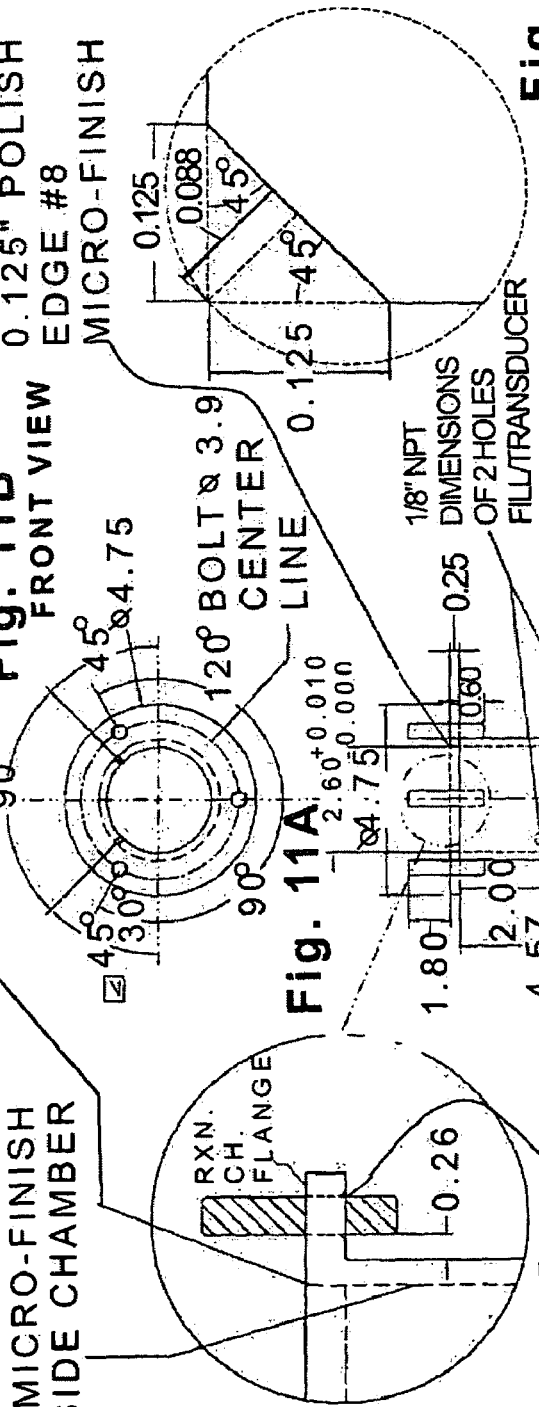
Figure 12:
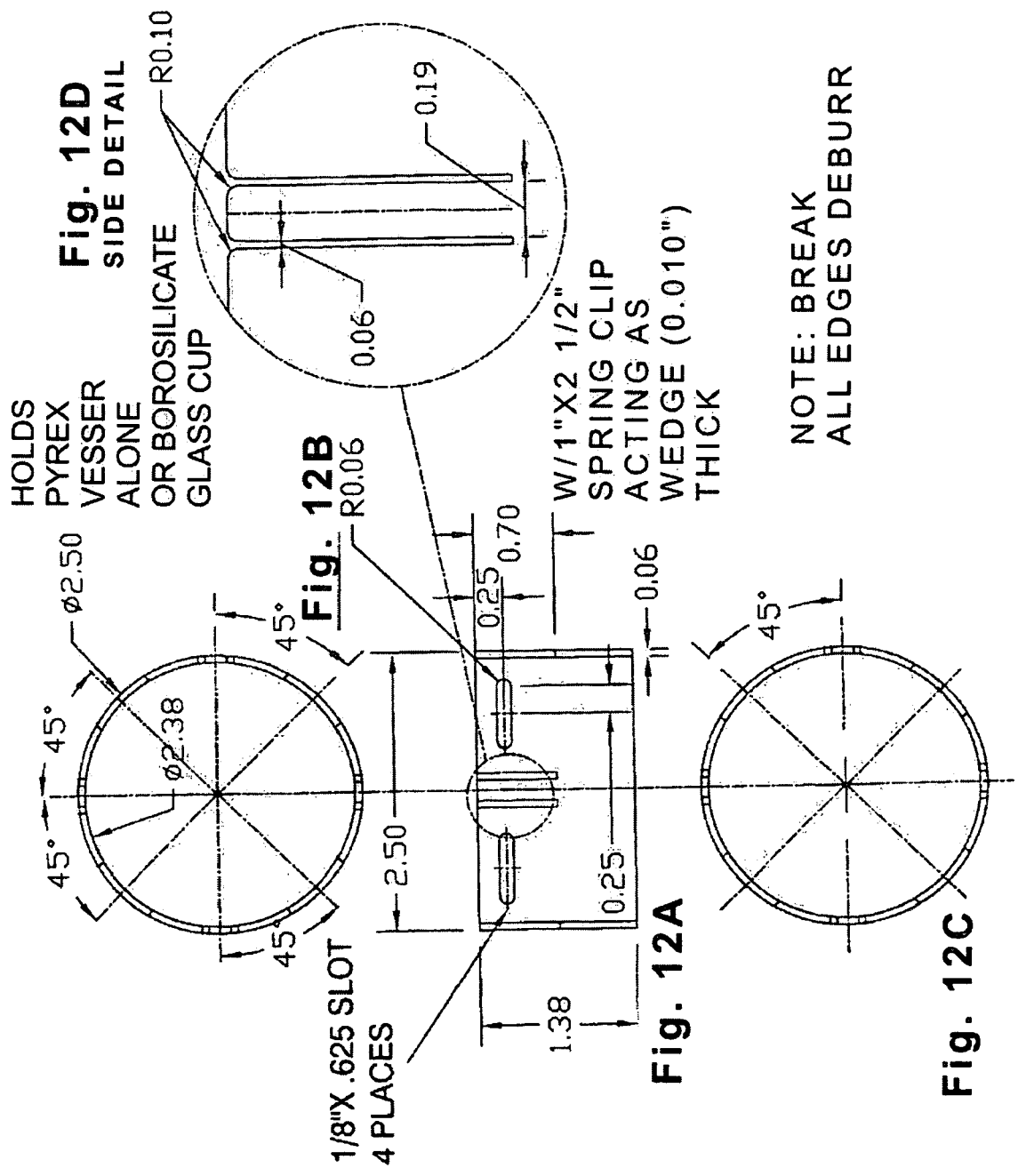
Figure 13:
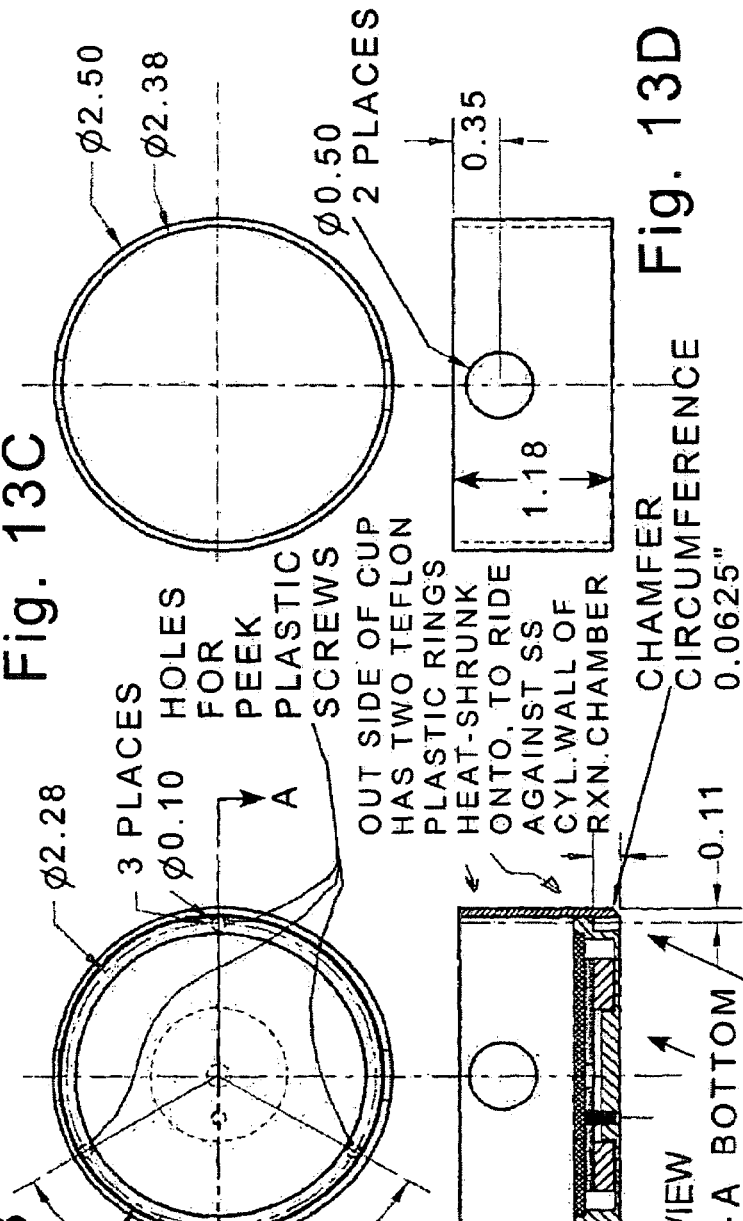

As alluded to above, the vessel 40 may be the rotating component 30 to the vessel (FIGS. 1, 2). As a preferable alternative, the vessel 40 may be an insert for the component 30 (FIGS. 2, 3, 5, 6-46). Preferably, as noted, the vessel 40 is a reaction vessel such as made of an inert material, for example, glass. In ASTM D-4742 (TFOUT) testing the vessel 40 can be in a form of a small PYREX glass dish having a plurality of liquid reaction component portions, say, four, and so on (FIGS. 27A-D); and in ASTM D-2272 (RBOT) testing, the vessel 40 can be in a form of a taller borosilicate glass cup, which may be provided with an inert coating such as a red ion-type coating formed from a copper-containing paste that is smeared on the inside and/or outside wall and/or bottom surface(s), baked, and rinsed off, several coatings of which can render the coating to look nearly black, which is an enhanced heat-absorbing sample vessel that can provide for more efficiency and/or control of the temperature (FIGS. 36A-B). Such a glass cup 40 can be placed in an inner cup that may have a magnet to receive rotating magnetic force from the magnet driver 38D (FIGS. 12A-D, 13A-D, 29A-D, 35A-B, 37A-D) that can function as a primary rotating component 30 with or without a wedging spacer between the cup 30 and the vessel 40 but preferably with a chamber vessel top spacer in a form of a hollow cylinder, i.e., a "slug," 40S (FIG. 28A-C) or a chamber top, inverted cone 40T (FIG. 7) as may be desired or required to rotate therewith (FIGS. 45, 46).

Typically, provided further are controls, which may be present in one or more control panels (FIGS. 5-7, 20A-B, 21A-B, 22A-B, 39-44), and which may be manually and/or electronically operated. Electronically operated controls may be analog and/or digital, and so forth and the like. Wireless communication of a bomb property (FIG. 44) may provide even more efficiency and/or control in the practice of the invention.

Some commercial specifications (QUANTUM device) are provided:

SOME COMMERCIAL EMBODIMENT TYPE

SPECIFICATIONS for a Tannas 'Quantum' Device TFOUT—Thin-Film Oxygen Uptake Test RPVOT—Rotating Pressure Vessel Oxidation Test (a.k.a. RB0T)

Principle:
  Test oil-catalyst mixture exposed as a thin film of oxygen at moderate pressure and at a test temperature until the oxygen destroys the oxidation resistance of the test oil. At this point the pressure drops rapidly and shows the oxidation induction time or break point.

Special Features & Benefits:
  New direct 'Dry Cylinder' sample heating approach does away with hot, hazardous, liquid bath mess and odor.
  Does not require placement of instrument in a hood to control objectionable oxidized oil odors.
  Simple venting technique permits discharge of objectionable odors through plastic tubing to scrubber, or distant hood.
  Has comparatively very small, bench-top, footprint.
  Front-loading, easily accessible pressure chamber.
  Convenient, front mounted oxygen charge and release valves.
  Each unit is a "stand-alone" but can be grouped if desired.
  Less downtime between test runs and quick interchangeability between TFOUT & RPVOT test methods.
  Rapid turn-around in test capabilities due to independent nature of each unit—estimated to at least double productivity with multi-rig setup.

Significance:
  TFOUT
  Useful for screening formulated oils prior to expensive engine testing.
  Useful condition monitoring tool for determining the remaining oxidation resistance of 'used' engine oils.
  Useful quality control tool in accessing the continued efficiency of catalysts in the process of manufacturing lubricating base oils, especially for re-refined base oils.
  Correlates to IIID and IIIE Engine Sequence Tests with appropriate catalyst packages. (Tannas is the only recognized commercial supplier of TFOUT Catalyst Packages.)
  Can be extended to other lubrication research applications where oxidation is a problem. RPVOT
  Used in evaluating the oxidation stability of new and in-service turbine oils having the same composition.
  Useful for assessing the remaining oxidation test life of in-service oils.

Dimensions:
  Bench-top footprint: 8"w×15"d×12"h (20×38×30.5 cm), ~20 lbs. (9 kg)

Voltage:
  120 VAC, Single Phase, 15 Amp. 50/60 Hz. (Also available in 220 VAC, 50 or 60 Hz)

Heating Medium:
  'Dry Cylinder' heating system—no hot oil bath.

Testing Capacity:
  Single position stainless steel oxidation vessel with pressure transducer.
  Designed for multiple unit (side-by-side) alignment on the bench-top, each functioning independently.

Test Parameter Capabilities:
  Temperature—Choice of operating temperatures (200±0.1° C. recommended maximum)
  Oxygen Charge—Choice of pressure (100±0.1 psi recommended maximum)
  Vessel Rotation—Variable speed control Read-out:
  Temperature controller and pressure meter mounted on cabinet front for easy viewing of parameters throughout test—no separate console box.
  Continuous temperature and oxygen pressure output through 9-pin Dsub connector.

TFOUT Test Parameters (D 4742):
  Operating Temperature: 160° C.
  Oxygen Charge: 90 psig (620 kPa)
  Oxidation Vessel Rotation: 100 RPM
  Oxidation Vessel Angle: 30°
  Test Sample: 1.500±0.001 g
  Catalyst Packages: Catalyst A—For correlation with engine oil Test Sequence IIID Catalyst B—For correlation with engine oil Test Sequence IIIE ps RPVOT Test Parameters (D 2272):
  Operating Temperature: 150° C.
  Oxygen Charge: 90 psi (620 kPa)
  Oxidation Vessel Rotation: 100 RPM
  Oxidation Vessel Angle: 30°
  Test Sample: 50±0.5 g
  Catalyst Components: Copper Wire Coil, Reagent Water Safety:
  Oxidation vessel tested under pressures of 500 psig (3450 KPa)—300% of maximum test pressure
  Current limiting fuses
  Over-pressure sensor & relief
  Over-temperature cut-out fuse Test Methods/Specifications:
  ASTM D 4742
  ASTM D 2272

CONCLUSION TO THE INVENTION

The present invention is thus provided. Various features, parts, subcombinations and combinations can be employed with or without reference to other features, parts, subcombination or combinations in the practice of the invention, and numerous adaptations and modifications can be effected within its spirit, the literal claim scope of which is particularly pointed out as follows:

What is claimed is:

1. A rotatable bomb device comprising:
   a housing with a hollow interior for receipt of a rotatable component to a vessel, with support for the rotatable component in the interior; and
   in the housing, the rotatable component,
   wherein the rotatable component is or includes an inner container that will be rotated by magnetic interaction of a magnet which is coupled to the rotatable compnent the inner container and a rotating magnet driver outside the hollow interior.

2. The device of claim 1, which can receive as the rotatable component, simultaneously or at separate times, separate rotatable component(s) in the hollow interior, each adapted for a predetermined test and/or reaction.

3. The device of claim 2, wherein the inner container holds or mounts a reaction dish adapted for oxygen uptake testing.

4. The device of claim 3, wherein a spacing slug is provided to reside above the reaction dish.

5. The device of claim 2, wherein the inner container holds or mounts a reaction cup adapted for oxygen uptake testing.

6. The device of claim 5, wherein an inverted top cone is provided to reside above the reaction cup.

7. The device of claim 5, wherein the reaction cup is a borosilicate glass treated to be darkened to enhance heat absorption.

8. The device of claim 6, wherein the reaction cup is a borosilicate glass treated to be darkened to enhance heat absorption.

9. The device of claim 1, further comprising a contrivance for wireless signaling of a property in the bomb.

10. The device of claim 1, wherein a substantially cylindrical wall defines a side boundary of the hollow interior, and a truncation substantially orthogonal thereto defines a bottom boundary of the hollow interior.

11. The device of claim 10, wherein said side and bottom boundaries provide a gliding support surface for rotation of the rotatable component to a vessel.

12. The device of claim 10, which can receive as the rotatable component separate rotatable component(s) in the hollow interior, simultaneously or at separate times, each adapted for a predetermined test and/or reaction.

13. The device of claim 12, wherein the inner container holds or mounts a glass reaction dish adapted for oxygen uptake testing.

14. The device of claim 12, wherein the inner container holds or mounts a glass reaction cup adapted for oxygen uptake testing.

15. The device of claim 14, wherein the glass reaction cup embraces a borosilicate glass cup having a substantially circular bottom connected to a substantially cylindrical wall that rises above the bottom, and an annular, inwardly projecting knobbed lip, wherein a substantial portion of a surface of the cup embraces an ion type heat-absorbing treatment that does not interfere substantially with the oxygen uptake testing.

16. The device of claim 15, wherein the heat-absorbing treatment appears to the eye to be essentially black, and is substantially inert to the oxygen uptake testing when applied to an inside surface of the glass reaction cup.

17. A reaction vessel for oxygen uptake testing, which comprises a borosilicate glass cup having a substantially circular bottom connected to a substantially cylindrical wall that rises above the bottom, and an annular, inwardly projecting knobbed lip, wherein a substantial portion of a surface of the cup embraces an ion type heat-absorbing treatment that does not interfere substantially with the oxygen uptake testing, and wherein the vessel can rotate in the oxygen uptake testing about an axis about center of the substantially cylindrical wall.

18. The vessel of claim 17, wherein said treatment appears to the eye to be essentially black, and is substantially inert to the oxygen uptake testing when applied to an inside surface of the vessel.

* * * * *